US010888598B2

(12) United States Patent
Simmons et al.

(10) Patent No.: US 10,888,598 B2
(45) Date of Patent: *Jan. 12, 2021

(54) EFFICIENT LIPID DELIVERY TO HUMAN TEAR FILM USING A SALT-SENSITIVE EMULSION SYSTEM

(71) Applicant: Allergan, Inc., Irvine, CA (US)

(72) Inventors: Peter A. Simmons, Yorba Linda, CA (US); Joseph G. Vehige, Laguna Niguel, CA (US)

(73) Assignee: ALLERGAN, INC., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/878,259

(22) Filed: Jan. 23, 2018

(65) Prior Publication Data

US 2018/0369311 A1 Dec. 27, 2018

Related U.S. Application Data

(63) Continuation of application No. 15/078,377, filed on Mar. 23, 2016, now Pat. No. 9,907,826, which is a continuation-in-part of application No. 13/708,771, filed on Dec. 7, 2012, now Pat. No. 9,314,528, and a continuation-in-part of application No. 13/708,783, filed on Dec. 7, 2012, now abandoned.

(60) Provisional application No. 61/625,401, filed on Apr. 17, 2012, provisional application No. 61/568,089, filed on Dec. 7, 2011.

(51) Int. Cl.

| A61K 31/341 | (2006.01) |
|---|---|
| A61K 31/205 | (2006.01) |
| A61K 31/7004 | (2006.01) |
| A61K 31/717 | (2006.01) |
| A61K 36/47 | (2006.01) |
| A61K 47/26 | (2006.01) |
| A61K 47/32 | (2006.01) |
| A61K 9/00 | (2006.01) |
| A61K 9/107 | (2006.01) |
| A61K 31/047 | (2006.01) |
| A61K 47/44 | (2017.01) |

(52) U.S. Cl.
CPC ............ *A61K 36/47* (2013.01); *A61K 9/0048* (2013.01); *A61K 9/1075* (2013.01); *A61K 31/047* (2013.01); *A61K 31/205* (2013.01); *A61K 31/341* (2013.01); *A61K 31/7004* (2013.01); *A61K 31/717* (2013.01); *A61K 47/26* (2013.01); *A61K 47/32* (2013.01); *A61K 47/44* (2013.01)

(58) Field of Classification Search
CPC .. A61K 31/047; A61K 31/205; A61K 31/341; A61K 31/717; A61K 31/7004; A61K 2300/00
See application file for complete search history.

(56) References Cited

U.S. PATENT DOCUMENTS

| 3,278,447 A | 10/1966 | McNicholas et al. |
|---|---|---|
| 4,201,706 A | 5/1980 | Trager et al. |
| 4,649,047 A | 3/1987 | Kaswan |
| 4,839,342 A | 6/1989 | Kaswan |
| 5,037,851 A | 8/1991 | Cavazza |
| 5,145,871 A | 9/1992 | Cavazza |
| 5,192,535 A | 3/1993 | Davis et al. |
| 5,411,952 A | 5/1995 | Kaswan |
| 5,432,199 A | 7/1995 | Cavazza |
| 5,474,979 A | 12/1995 | Ding et al. |
| 5,527,831 A | 6/1996 | Franz et al. |
| 5,827,512 A | 10/1998 | Gleich |
| 5,981,607 A | 11/1999 | Ding et al. |
| 6,156,293 A | 12/2000 | Jutila et al. |
| 6,193,957 B1 | 2/2001 | Ahmed |
| 6,228,392 B1 | 5/2001 | Morcos et al. |
| 6,274,725 B1 | 8/2001 | Sanghvi et al. |
| 6,365,622 B1 | 4/2002 | Cavazza |
| 6,555,526 B2 | 4/2003 | Matsuo et al. |
| 6,585,987 B1 | 7/2003 | Fransoni |
| 6,635,654 B1 | 10/2003 | Chang et al. |
| 7,045,121 B2 | 5/2006 | Chang et al. |
| 7,659,270 B2 | 2/2010 | Bachand et al. |
| 8,211,855 B2 | 7/2012 | Chang et al. |
| 8,496,976 B2 | 7/2013 | Gore et al. |
| 8,569,367 B2 | 10/2013 | Vehige et al. |
| 8,569,370 B2 | 10/2013 | Vehige et al. |
| 8,729,125 B2 | 5/2014 | Vehige et al. |
| 8,957,048 B2 | 2/2015 | Vehige et al. |
| 2002/0002185 A1 | 1/2002 | Reed et al. |
| 2002/0071874 A1 | 6/2002 | Olejnik et al. |
| 2003/0069410 A1 | 4/2003 | Ravikumar |
| 2003/0190258 A1 | 10/2003 | Smith |
| 2003/0195160 A1 | 10/2003 | Smith |
| 2004/0137079 A1 | 7/2004 | Cook et al. |

(Continued)

FOREIGN PATENT DOCUMENTS

| EP | 0028110 | 5/1981 |
|---|---|---|
| EP | 0436726 | 7/1990 |

(Continued)

OTHER PUBLICATIONS

Albietz, Julie et al, A Comparison of the Effect of Refresh plus and Bion Tears on Dry Eye Symptoms and Ocular Surface Health in Myopic LASIK Patients, the CLAO Journal, 2002, 96-100, 28(2).

Alfieri, Roberta et al, Compatible Osmolytes Modulate the Response of Porcine Endothelial Cells to Hypertonicity and Protect Them From Apoptosis, J. Physiol., 2002, 499-508, 540.

Barker, Robert et al, Acidic Polyamino Acids Inhibit Human Eosinophil Granule Major Basic Protein Toxicity. Evidence of a Functional Role for ProMBP, J. Clin. Invest., Sep. 1991, 798-805, 88.

(Continued)

*Primary Examiner* — Zohreh A Fay
(74) *Attorney, Agent, or Firm* — Lorenz Siddiqi

(57) ABSTRACT

Provided herein are low salt ophthalmic pharmaceutical composition and methods of use thereof, for example, in the treatment of dry eye syndrome.

19 Claims, 7 Drawing Sheets

(56) References Cited

U.S. PATENT DOCUMENTS

| | | |
|---|---|---|
| 2004/0192647 A1 | 9/2004 | Babizhayev |
| 2005/0009836 A1 | 1/2005 | Laskar et al. |
| 2006/0035842 A1 | 2/2006 | Tsuzuki et al. |
| 2006/0106104 A1 | 5/2006 | Vehige et al. |
| 2007/0015694 A1 | 1/2007 | Chang et al. |
| 2007/0015960 A1 | 1/2007 | Gornert et al. |
| 2008/0026991 A1 | 1/2008 | Rabinovich-Giulatti et al. |
| 2008/0070834 A1 | 3/2008 | Chang et al. |
| 2008/0207495 A1 | 8/2008 | Graham et al. |
| 2010/0184664 A1 | 7/2010 | Simmons et al. |
| 2012/0201910 A1 | 8/2012 | Gore et al. |
| 2013/0150324 A1 | 6/2013 | Simmons et al. |

FOREIGN PATENT DOCUMENTS

| | | |
|---|---|---|
| EP | 0778021 | 6/1997 |
| EP | 0848952 | 6/1998 |
| EP | 1044678 | 3/2003 |
| JP | 2763400 | 3/1998 |
| JP | 2009501228 | 1/2009 |
| JP | 2010500414 | 1/2010 |
| JP | 2010-036255 | 2/2010 |
| RU | 2216342 | 11/2003 |
| RU | 2234337 | 8/2004 |
| TW | 201316984 | 5/2013 |
| WO | 1998-041208 | 9/1998 |
| WO | 0029030 | 5/2000 |
| WO | 0157172 | 8/2001 |
| WO | 2002-038161 | 5/2002 |
| WO | 03004512 | 1/2003 |
| WO | 03028633 | 4/2003 |
| WO | 2003-051332 | 6/2003 |
| WO | 2004006801 | 1/2004 |
| WO | 2004030666 | 4/2004 |
| WO | 2004-084877 | 7/2004 |
| WO | 2006055454 | 5/2006 |
| WO | 2007008894 | 1/2007 |
| WO | 2008027341 | 3/2008 |
| WO | 2008-106228 A2 | 9/2008 |
| WO | 2010-047927 | 4/2010 |
| WO | 2010141648 | 12/2010 |
| WO | 2011042794 A3 | 6/2011 |
| WO | 2013052760 | 4/2013 |

OTHER PUBLICATIONS

Becton Dickinson Gmbh, "BD☐ Buffered Sodium Chloride-Peptone Solution pH 7.0 BD Buffered Sodium Chloride Peptone Solution + Polysorbate 80", BA-257086.02, 2011, pp. 1-3, retrieved from http://www.bd.com/resource.aspx?IDX=23327.

Bielory, L., Allergic and Immunologic Disorders of the Eye. Part II: Ocular Allergy, J. Allergy CLin. Immunol. 2000, 106: 1019-1035.

Biocompare®: Product Review: Upstate's Beadlyte Human/Mouse Cytokine Detection Kits, Jun. 15, 2004, 3 Pages, Biocompare, Inc.

Brown, Theodore et al, Glossary: Salt, Chemistry: The Central Science, 2006, G-10, 10th Edition.

Burg, Maurice, Molecular Basis of Osmotic Regulation, American Physiological Society, 1995, F983-F996, 268.

Cammarata, Patrick et al, Osmoregulatory Alterations in taurine Uptake by Cultured Human and Bovine lens Epithelial Cells, Invest. Ophthalmol. Vis. Sci., 2002, 425-433, 43.

Gilbard, Jeffrey, Tear Film Osmolarity and Keratoconjunctivitis Sicca, the CLAO Journal, Jul. 1985, 243-250, 11 (3).

Glossary of Medical Education Terms, retrieved from http://www.iime.org/glossary.htm#P[Mar. 14, 2013 10:18:14 AM] on Mar. 14, 2013, 23 pages.

Hom, et al., Understanding Emulsion Eye Drop Technology, Review of Optometry, 2008, 5 pages, http:www.revoptom.com/index.asppage+2_888.htm, US.

International Search Report & Written Opinion dated Jun. 7, 2006 for PCT/US05/41064 filed Nov. 14, 2005 in the name of Allergan, Inc.

Jumaa, et al., Mixture experiments with the oil phase of parenteral emulsions, European Journal of Pharmaceutics and Biopharmaceutics, 1998, 161-167, 46, US.

Jumaa, et al., The effect of oil components and homogenization conditions on the physicochemical properties and stability of parenteral fat emulsions, International Journal of Pharmaceutics, 1998, 81-89, 163, US.

Khanal, Santoush, et al., Effect of an Oil-in-Water Emulsion on the Tear Physiology of Patients with Mild to Moderate Dry Eye, Cornea, Feb. 2007, 175-181, vol. 26, No. 2, Lippincott Williams & Wilkins.

Matsuo, Toshihiko et al, Trehalose Eye Drops in the Treatment of Dry Eye Syndrome, Ophthalmology, 2002, 2024-2029, 109.

McGrogan, Michael et al, Isolation of a Complementary DNA Clone Encoding a Precursor to Human Eosinophil Major Basic Protein, J. Exp. Med., Dec. 1988, 2295-2308, 168.

Mohammad-Ali Javadi, Dry Eye Syndrome, Journal of ophthalmology Visual Research, 2011, 192-198, 6 (3).

Nakajima, Toshiharu et al, Gene Expression Screening of Human Mast Cells and Eosinophils Using High-Density Oligonucleotide Probe Arrays: Abundant Expression of Major Basic Protein in Mast Cells, Blood, Aug. 2001, 1127-1134, 98 (4).

Patent Cooperation Treaty, Notification of Transmittal of the International Search Report and the Written Opinion of theInternational Searching Authority, or the Declaration, Form PCT/ISA/220, Int. App. No. PCT/US2012/058893, dated Dec. 3, 2012.

Peluso, Gianfranco et al, Carnitine: An Osmolyte That Plays a Metabolic Role, Journal of Cellular Biochemistry, 2000, 1-10, 80.

Pessotto, P. et al, The Presence of L-Carnitine in Ocular Tissues of the Rabbit, Journal of Ocular Pharmacology, 1994, 643-651, 10 (4).

Polysorbate 80, Wikipedia entry, retrieved from http://en.wikipedia.org/wiki/Polysorbate_80 on Feb. 10, 2015.

Popken-Harris, Pamela et al, Biochemical Properties, Activities, and Presence in Biologic Fluids of Eosinophil Granule Major Basic Protein, J. Allergy Clin. Immunol., 1994, 1282-1289, 94 (6).

Popken-Harris, Pamela et al, Regulation and Processing of a Precursor Form of Eosinophil Granule Major Basic Protein (ProMBP) in Differentiating Eosinophils, Blood, Jul. 1998, 623-631, 92 (2).

Rashid, et al., Topical Omega-3 and Omega-6 Fatty Acids for Treatment of Dry Eye, Arch Ophthalmol, 2008, 219-225, 126, Laboratory Sciences, US.

Rhyne, P.W. et al, Analysis of Apoptotic Cells Using Beadlyte Suspension Arrays, Biotechniques, Sep. 2003, 624-629 (Abstract), 35 (3).

Shioda, Ryo et al, Osmosensitive Taurine Transporter Expression and Activity in Human Corneal Epithelial Cells, Investigative Ophthalmology & Visual Science, Sep. 2002, 2916-2922, 43 (9).

Database WPI, Week 198140, Thomson Scientific, London, GB (2 pages).

Vieira, et al., Effect of ricinoleic acid in acute and subchronic experimental models of inflammation, Mediators of Inflammation, 2000, 223-228, 9, Taylor & Francis Ltd.

Voet et al, Transport Across the Mitochondrial Membrane, Biochemistry, 1990, 622.

EFFICIENT LIPID DELIVERY TO HUMAN TEAR FILM USING A SALT-SENSITIVE EMULSION SYSTEM

CROSS-REFERENCES TO RELATED APPLICATIONS

This application is a continuation of U.S. patent application Ser. No. 15/078,377, filed Mar. 23, 2016, which is a continuation-in-part of U.S. patent application Ser. No. 13/708,771 filed Dec. 7, 2012, now U.S. Pat. No. 9,314,528, issued Apr. 19, 2016, which in turn claims priority to U.S. Provisional Application Ser. Nos. 61/568,089, filed Dec. 7, 2011 and 61/625,401 filed Apr. 17, 2012, the disclosures of which are hereby incorporated in their entireties herein by reference. U.S. patent application Ser. No. 15/078,377 is also a continuation-in-part of U.S. patent application Ser. No. 13/708,783, filed Dec. 7, 2012, now abandoned, which in turn claims priority to U.S. Provisional Application Ser. Nos. 61/568,089, filed Dec. 7, 2011 and 61/625,401 filed Apr. 17, 2012, the disclosures of which are hereby incorporated in their entireties herein by reference.

BACKGROUND OF THE INVENTION

The present application relates to compositions and methods to supplement and enhance the native tear film of the eye, e.g., the native lipid layer of the tear film. The compositions and methods disclosed herein provide inter alia relief of hyperosmotic stress and other conditions associated with dry eye syndrome.

Delivering therapeutic agents, e.g., therapeutic lipids, to supplement and enhance the native tear film is a recognized strategy in treating symptoms of dry eye syndrome. Without wishing to be bound by any theory, it is believed that this strategy is especially advantageous under conditions of low humidity or when other factors increase tear film evaporation. In dry eye syndrome, loss of water in the tear film can lead to increased salt content at the ocular surface, which in turn can lead to hyperosmotic stress to the cells of the ocular surface. It is further believed that the native lipid layer of the tear film functions inter alia to reduce evaporation from the underlying aqueous tear film layer. Accordingly, in cases where the native lipid layer is reduced, e.g., in disorders or conditions described herein or known in the art, it is believed that supplementation and enhancement of the lipid layer of the tear film is beneficial.

The lipid layer of the native tear film is quite thin (i.e., 0.1-0.2 micron). Moreover, the total volume of lipid in the tear film is but a small fraction of the total tear film volume. Thus, previous methods of supplementation and enhancement of the structure and function of the lipid layer of the tear film by topical application of a lipid-containing pharmaceutical composition require merely a small therapeutically effective volume of lipid to be delivered. In such methods, however, excess lipid provided during instillation can displace and disrupt the aqueous component of the tear film. Because the lipid delivered by such methods needs to become established as part of the native lipid layer, at the air interface over the aqueous tear, methods which reduce the aqueous layer of the tear film can afford reduced effectiveness. Moreover, any topical drop delivery method of supplementation and enhancement of the lipid layer of the tear film requires rapid delivery during the brief contact time of the topical eye drop with the ocular surface.

Thus, previous methods of supplementing and enhancing the lipid layer of the tear film have been addressed by a variety of approaches, including using a substantial amount of lipid (e.g., 1-5%) and/or building an emulsion system that readily separates. However, such methods suffer multiple disadvantages, including a requirement for shaking of the composition prior to instillation, reduced clarity of the composition upon instillation, variability of the total volume of lipid delivered to the eye, and problems with tolerability vis-a-vis aqueous eye drops.

Typical symptoms of keratoconjunctivitis or dry eye include feelings of dryness, burning, and a sandy-gritty eye sensation that can worsen during the day. Symptoms may also be described as itchy, scratchy, stingy or tired eyes. Other symptoms include pain, redness, a pulling sensation, and pressure behind the eye. The damage to the eye surface resulting from dry eye increases discomfort and sensitivity to bright lightand both eyes usually are affected.

Because blinking coats the eye with tears, symptoms are worsened by activities in which the rate of blinking is reduced due to prolonged use of the eyes. These activities include prolonged reading, computer usage, driving or watching television. Symptoms increase in windy, dusty or smoky areas, in dry environments, high altitudes including airplanes, on days with low humidity, and in areas where an air conditioner, fan, or heater, is being used. Symptoms are less severe during cool, rainy, or foggy weather, and in humid places. Most people who have dry eyes experience mild irritation with no long-term effects. However, if the condition is left untreated or becomes severe, it can produce complications that can cause eye damage, resulting in impaired vision or possibly in the loss of vision.

Having dry eyes for a prolonged period of time can lead to tiny abrasions on the surface of the eyes. In advanced cases, the epithelium undergoes pathologic changes, namely squamous metaplasia and loss of goblet cells sometimes due to activation of T cells acting against those cells. Some severe cases result in thickening of the corneal surface, corneal erosion, punctate keratopathy, epithelial defects, corneal ulceration, corneal neovascularization, corneal scarring, corneal thinning, and even corneal perforation. An abnormality of any one of the three layers of tears which produces an unstable tear film, may result in symptoms of keratitis sicca.

Keratoconjunctivitis sicca is usually due to inadequate tear production. The aqueous tear layer is affected, resulting in aqueous tear deficiency or lacrimal hyposecretion. The lacrimal gland does not produce sufficient tears to keep the entire conjunctiva and cornea covered by a complete layer. This usually occurs in people who are otherwise healthy. Increased age is associated with decreased tearing. This is the most common type found in postmenopausal women. Causes include idiopathic, congenital alacrima, xerophthalmia, lacrimal gland ablation, and sensory denervation. In rare cases, it may be a symptom of collagen vascular diseases, including rheumatoid arthritis, Wegener's granulomatosis, and systemic lupus erythematosus. Sjögren's syndrome and autoimmune diseases associated with Sjögren's syndrome are also conditions associated with aqueous tear deficiency. Drugs such as isotretinoin, sedatives, diuretics, tricyclic antidepressants, antihypertensives, oral contraceptives, antihistamines, nasal decongestants, beta-blockers, phenothiazines, atropine, and pain-relieving opiates such as morphine can cause or worsen this condition. Infiltration of the lacrimal glands by sarcoidosis or tumors, or postradiation fibrosis of the lacrimal glands can also cause this condition.

Keratoconjunctivitis sicca can also be caused by abnormal tear composition resulting in rapid evaporation or premature destruction of the tears. When caused by rapid evaporation, it is termed evaporative dry eyes. In this condition, although the tear gland produces a sufficient amount of tears, the rate of evaporation of the tears is too rapid. There is a loss of water from the tears that results in tears that are too "salty" or hypertonic. As a result, the entire conjunctiva and cornea cannot be kept covered with a complete layer of tears during certain activities or in certain environments.

Aging is one of the most common causes of dry eyes. This is due to the fact that tear production decreases with age. It may be caused by thermal or chemical burns, or by adenoviruses. Diabetics are also at increased risk for dry eye.

An eye injury or other problem with the eyes or eyelids, such as bulging eyes or a drooping eyelid, can cause keratoconjunctivitis sicca. Disorders of the eyelid can impair the complex blinking motion required to spread tears.

About half of all people who wear contact lenses have dry eyes. This is because soft contact lenses, which float on the tear film that covers the cornea, absorb the tears in the eyes.

Dry eye also occurs or gets worse after refractive surgeries, in which the corneal nerves are cut during the creation of a corneal flap, because the corneal nerves stimulate tear secretion. Dry eyes caused by these procedures usually disappear after several months.

Abnormalities of the lipid tear layer caused by blepharitis and rosacea and abnormalities of the mucin tear layer caused by vitamin A deficiency, trachoma, diphtheric keratoconjunctivitis mucocutaneous disorders and certain topical medications may cause dry eye or keratoconjunctivitis sicca.

Dry eyes can usually be diagnosed by the symptoms alone. Tests can determine both the quantity and the quality of the tears. A slit lamp examination can be performed to diagnose dry eyes and to document any damage to the eye. A Schirmer's test can measure the amount of moisture bathing the eye. This test is useful for determining the severity of the condition.

A variety of approaches can be taken to treatment, such as: avoidance of exacerbating factors, tear stimulation and supplementation, increasing tear retention, and eyelid cleansing and treatment of eye inflammation. For mild and moderate cases, supplemental lubrication is the most important part of treatment. Application of artificial tears every few hours can provide temporary relief.

Lubricating tear ointments can be used during the day, but they generally are used at bedtime due to poor vision after application. They contain white petrolatum, mineral oil, and similar lubricants. They serve as a lubricant and an emollient. Depending on the severity of the condition, ointments may be applied from every hour to just at bedtime. Ointments should not be used with contact lenses. Inflammation occurring in response to tears film hypertonicity can be suppressed by mild topical steroids or with topical immunosuppressants such as cyclosporine.

The present invention provides, inter alia, compositions and methods directed to an alternate means of lipid release by the use of a salt-sensitive emulsion system in an ophthalmic pharmaceutical composition which is largely free of salt. Specifically, the present compositions employ a surfactant and a salt-sensitive viscosity modulating polymer to hold a therapeutic lipid (e.g., castor oil) in a stable sub-micron emulsion. When instilled in the eye, the composition mixes with the native tear film, the natural salt content of which is sufficient to cause a rapid decrease in viscosity due to changes in the salt-sensitive viscosity modulating polymer. Upon loss of viscosity, therapeutic lipid is released from the sub-micron emulsion at the eye, thereby providing supplementation and enhancement of the native lipid layer of the tear film.

SUMMARY OF THE INVENTION

In a first aspect, there is provided a low salt ophthalmic pharmaceutical composition which includes a sub-micron emulsion, a polymer lubricant, and a salt-sensitive viscosity modulating polymer, wherein the sub-micron emulsion includes a surfactant and a therapeutic lipid.

In another aspect, there is provided a low salt ophthalmic pharmaceutical composition including: castor oil at a concentration of about 0.25% (w/w); polysorbate 80 at a concentration of about 0.5% (w/w); acrylate/$C_{10}$-$C_{30}$ acrylate crosspolymer at a concentration of about 0.1% (w/w), wherein said acrylate/$C_{10}$-$C_{30}$ acrylate crosspolymer has a standard emulsion viscosity between 1,700 and 4,500 cPs; carboxymethylcellulose sodium at a concentration of about 0.5% (w/w); glycerin at a concentration of about 1.0% (w/w); a stabilized oxychloro complex preservative at a concentration of about 0.01% (w/w); boric acid at a concentration of about 0.6% (w/w); erythritol at a concentration of about 0.25% (w/w); levocarnitine at a concentration of about 0.25% (w/w); NaOH; and water.

In another aspect, there is provided a method for treating dry eye syndrome. The method includes administering to a subject in need of treatment of dry eye syndrome a low salt ophthalmic pharmaceutical composition as described herein, thereby treating the dry eye syndrome.

TABLE I

| | | | |
|---|---|---|---|
| [1] POLYSORBATE 80 Grade: NF ph Eur | 0.5 | % w/w | Active |
| [2] CARBOXYMETHYLCELLULOSE SODIUM (LOW VISCOSITY 7LFPH) Grade: Ph Eur USP | 0.5 | % w/w | Active |
| [3] GLYCERIN Grade: Ph Eur USP | 1.0 | % w/w | Active |
| [4] PURITE Grade: | 0.01 | % w/w | Preservative |
| BORIC ACID Grade: NF Ph Eur | 0.6 | % w/w | Buffer |
| [5] PEMULEN TR-2 Grade: NF | 0.1 | % w/w | Stabilizer |
| [6] CASTOR OIL Grade: Eur Ph USP | 0.25 | % w/w | Excipient |
| ERYTHRITOL Grade: NF Ph Eur | 0.25 | % w/w | Excipient |
| LEVOCARNITINE Grade: Ph Eur USP | 0.25 | % w/w | Excipient |
| [7] SODIUM HYDROXIDE Grade: NF Ph Eur | 7.3 | pH | pH Adjust |
| [8] WATER FOR INJECTION/ PURIFIED WATER Grade: USP | 100 | % w/w | QS Adjust |

[1] PM# 12783. Super Refined Polysorbate 80 from CRODA. Primary emulsifer and demulcent.
[2] Demulcent
[3] Demulcent and tonicity agent
[4] Stabilized Oxychloro Complex (Purite). Add by assay value.
[5] Pemulen TR-2NF (Carbomer Copolymer Type A, Tested to Ph Eur). Secondary emulsifer.
[6] Lipophilic vehicle
[7] pH target 7.3
[8] Hydrophilic vehicle The Table I formulation includes the concentrations of actives and/or excipients as disclosed above which can be in concentrations which vary from what is stated above. The variation may be such that the amounts are "about" what is stated above so long as that amount would be found bioequivalent by a regulatory agency such as the FDA or the EMEA.

The formulation may be preserved or non-preserved (not containing Purite®), such as a unit dose version. This version would be the same as that in Table 1 except it would contain no Purite®.

Some embodiments of the invention are included in the following paragraphs:

1) A composition useful as an artificial tear, which is a salt free emulsion comprising castor oil and specifically excludes olive oil and contains at least one active agent selected from the group consisting of polysorbate, carboxymethylcellulose and glycerine.
2) The composition of paragraph 1 wherein said mixture comprises from about 0.1%-0.5% w/w, castor oil.
3) The composition of paragraphs 1-2 wherein castor oil is the only oil in the emulsion.
4) The composition of paragraphs 1-3 wherein the castor oil is emulsified in an aqueous phase.
5) The composition of paragraph 4 wherein the castor oil is present in about 0.25% w/w.
6) The composition of paragraphs 4-5 further including a primary and a secondary emulsifier.
7) The composition of paragraphs 1-6 wherein the composition contains a preservative.
8) The composition of paragraph 7 wherein the preservative is selected from the group consisting of PURITE and benzalkonium chloride.
11. The composition of paragraph 8 wherein the preservative is PURITE is present in a concentration of about 0.01% w/v.
12. An emulsion for use in treating dry eye wherein the emulsion is salt-free and comprises castor oil, polysorbate 80, carboxymethylcellulose and glycerine.
13. The composition of paragraph 12 wherein the emulsion also contains the emulsifier pemulen.
14. The emulsion of paragraphs 12-13 further comprising erythritol and levocarnitine.
15. An emulsion for treating dry eye as shown in Tables I, II or III.
16. A method of treating dry eye comprising administration of any one of the compositions or emulsions of paragraphs 1-15.
17. A composition for the treatment of dry eye or keratoconjunctivitis sicca wherein the composition comprises about 0.5% w/w Polysorbate 80, about 0.5% w/w carboxymethylcellulose, about 1.0% w/w glycerine, about 0.6% w/w boric acid, about 0.1% w/w pemulen, about 0.25% w/w castor oil, about 0.25% w/w erythritol, about 0.25% w/w levocarnitine, sodium hydroxide to adjust the pH to about 7.3 and water.
18. The composition of paragraph 17 further comprising 0.01% Purite®.
19. The composition of paragraph 17 wherein the composition is applied topically to an eye which is suffering from dry eye.
20. The composition of paragraph 17 wherein the composition is applied topically to an eye to alleviate the symptoms of dry eye.
21. The composition of paragraph 17 wherein the composition is applied topically to an eye to prevent dry eye syndrome.
22. A low salt ophthalmic pharmaceutical composition comprising a sub-micron emulsion, a polymer lubricant, and a salt-sensitive viscosity modulating polymer, wherein said sub-micron emulsion comprises a surfactant and a therapeutic lipid.
23. The low salt ophthalmic pharmaceutical composition of paragraph 22, wherein said composition is clear.
24. The low salt ophthalmic pharmaceutical composition according to any one of paragraphs 21 to 23, wherein said therapeutic lipid is a fatty acid glyceride.
25. The low salt ophthalmic pharmaceutical composition according to paragraph 24, wherein said fatty acid glyceride is a castor oil, olive oil, peanut oil, corn oil, or sunflower oil.
26. The low salt ophthalmic pharmaceutical composition according to any one of paragraphs 22 to 25, wherein said therapeutic lipid is castor oil.
27. The low salt ophthalmic pharmaceutical composition according to paragraph 26, wherein said castor oil is present at a concentration between about 0.01% (w/w) and about 10% (w/w).
28. The low salt ophthalmic pharmaceutical composition according to paragraph 27, wherein said castor oil is present at a concentration of about 0.25% (w/w).
29. The low salt ophthalmic pharmaceutical composition according to any one of paragraphs 22 to 28, wherein said surfactant is a sorbitan ester.
30. The low salt ophthalmic pharmaceutical composition according to paragraph 29, wherein said surfactant is polysorbate 80.
31. The low salt ophthalmic pharmaceutical composition according to paragraph 30, wherein said polysorbate 80 is present at a concentration between about 0.01% (w/w) and about 1.0% (w/w).
32. The low salt ophthalmic pharmaceutical composition according to paragraph 31, wherein said polysorbate 80 is present at a concentration of about 0.5% (w/w).
33. The low salt ophthalmic pharmaceutical composition according to any one of paragraphs 22 to 32, wherein said salt-sensitive viscosity modulating polymer is an acrylate/C10-C30 acrylate crosspolymer.
34. The salt-sensitive viscosity modulating polymer according to paragraph 33 having a standard emulsion viscosity between 1,700 and 4,500 cPs.
35. The low salt ophthalmic pharmaceutical composition according to paragraph 34, wherein said salt-sensitive viscosity modulating polymer is present at a concentration between about 0.01% (w/w) and about 1.0% (w/w).
36. The low salt ophthalmic pharmaceutical composition according to paragraph 35, wherein said salt-sensitive viscosity modulating polymer is present at a concentration of about 0.1% (w/w).
37. The low salt ophthalmic pharmaceutical composition according to any one of paragraphs 22 to 36, wherein said polymer lubricant is a demulcent.
38. The low salt ophthalmic pharmaceutical composition according to paragraph 37, wherein said polymer lubricant is carboxymethylcellulose sodium present at a concentration between about 0.01% (w/w) and about 1.0% (w/w).
39. The low salt ophthalmic pharmaceutical composition according to paragraph 38, wherein said carboxymethylcellulose sodium is present at a concentration of about 0.5% (w/w).
40. The low salt ophthalmic pharmaceutical composition according to any one of paragraphs 22 to 39, further comprising a compatible solute.
41. The low salt ophthalmic pharmaceutical composition according to paragraph 40, wherein said compatible solute is a polyol or a zwitterionic amino acid.
42. The low salt ophthalmic pharmaceutical composition according to paragraph 41, wherein said compatible solute is erythritol or levocarnitine.

43. The low salt ophthalmic pharmaceutical composition according to paragraph 42, wherein said compatible solute is erythritol present at a concentration between about 0.01% (w/w) and about 1.0% (w/w).
44. The low salt ophthalmic pharmaceutical composition according to paragraph 42, wherein said compatible solute is levocarnitine present at a concentration between about 0.01% (w/w) and about 1.0% (w/w).
45. The low salt ophthalmic pharmaceutical composition according to paragraph 42, wherein said compatible solute is erythritol at a concentration of about 0.25% (w/w).
46. The low salt ophthalmic pharmaceutical composition according to paragraph 42, wherein said compatible solute is levocarnitine at a concentration of about 0.25% (w/w).
47. The low salt ophthalmic pharmaceutical composition according to paragraph 42 comprising erythritol at a concentration of about 0.25% (w/w) and levocarnitine at a concentration of about 0.25% (w/w).
48. The low salt ophthalmic pharmaceutical composition according to any one of paragraphs 22-47, further comprising a tonicity agent.
49. The low salt ophthalmic pharmaceutical composition according to paragraph 48, wherein said tonicity agent is a demulcent.
50. The low salt ophthalmic pharmaceutical composition according to paragraph 48, wherein said tonicity agent is glycerin present at a concentration between about 0.01% (w/w) and about 5.0% (w/w).
51. The low salt ophthalmic pharmaceutical composition according to paragraph 50, wherein said glycerin is present at a concentration of about 1.0% (w/w).
52. The low salt ophthalmic pharmaceutical composition according to any one of paragraphs 21-51, further comprising a preservative.
53. The low salt ophthalmic pharmaceutical composition according to paragraph 52, wherein said preservative is a stabilized oxychloro complex.
54. The low salt ophthalmic pharmaceutical composition according to paragraph 53, wherein said preservative is present at a concentration between about 0.001% (w/w) and about 0.1% (w/w).
55. The low salt ophthalmic pharmaceutical composition according to paragraph 53, wherein said preservative is present at a concentration of about 0.01% (w/w).
56. The low salt ophthalmic pharmaceutical composition according to any one of paragraphs 22 to 55, further comprising a buffer.
57. The low salt ophthalmic pharmaceutical composition according to paragraph 56, wherein said buffer is boric acid present at a concentration between about 0.01% (w/w) and about 1.0% (w/w).
58. The low salt ophthalmic pharmaceutical composition according to paragraph 57, wherein said boric acid is present at a concentration of about 0.6% (w/w).
59. The low salt ophthalmic pharmaceutical composition according to any one of paragraphs 22 to 38, further comprising a pH adjustment agent.
60. The low salt ophthalmic pharmaceutical composition according to paragraph 59, wherein said pH adjustment agent is NaOH.
61. The low salt ophthalmic pharmaceutical composition according to paragraph 59 having pH of about 7.3
62. The low salt ophthalmic pharmaceutical composition according to paragraph 60 comprising: castor oil at a concentration between about 0.01% (w/w) and about 10% (w/w); polysorbate 80 at a concentration between about 0.01% (w/w) and about 1.0% (w/w); acrylate/C10-C30 acrylate crosspolymer at a concentration between about 0.01% (w/w) and about 1.0% (w/w), wherein said acrylate/C10-C30 acrylate crosspolymer has a standard emulsion viscosity between 1,700 and 4,500 cPs; carboxymethylcellulose sodium at a concentration between about 0.01% (w/w) and about 1.0% (w/w); glycerin at a concentration between about 0.01% (w/w) and about 5.0% (w/w); a stabilized oxychloro complex preservative at a concentration between about 0.001% (w/w) and about 0.1% (w/w); boric acid at a concentration of about 0.6% (w/w); erythritol at a concentration of about 0.25% (w/w); levocarnitine at a concentration of about 0.25% (w/w); NaOH; and water.
63. A low salt ophthalmic pharmaceutical composition comprising: castor oil at a concentration of about 0.25% (w/w); polysorbate 80 at a concentration of about 0.5% (w/w); acrylate/C10-C30 acrylate crosspolymer at a concentration of about 0.1% (w/w), wherein said acrylate/C10-C30 acrylate crosspolymer has a standard emulsion viscosity between 1,700 and 4,500 cPs; carboxymethylcellulose sodium at a concentration of about 0.5% (w/w); glycerin at a concentration of about 1.0% (w/w); a stabilized oxychloro complex preservative at a concentration of about 0.01% (w/w); boric acid at a concentration of about 0.6% (w/w); erythritol at a concentration of about 0.25% (w/w); levocarnitine at a concentration of about 0.25% (w/w); NaOH; and water.
64. A method for treating dry eye syndrome comprising: administering to a subject in need of treatment of dry eye syndrome a low salt ophthalmic pharmaceutical composition according to any one of paragraphs 22 to 63; thereby treating said dry eye syndrome.
65. The method of paragraph 64, wherein said therapeutic lipid is castor oil at a concentration between about 0.01% (w/w) and about 10% (w/w).
66. The method of any one of paragraphs 64 to 65, wherein said surfactant is polysorbate 80 at a concentration between about 0.01% (w/w) and about 1.0% (w/w).
67. The method of any one of paragraphs 64 to 65, wherein said salt-sensitive viscosity modulating polymer comprises acrylate/C10-C30 acrylate crosspolymer present at a concentration between about 0.01% (w/w) and about 1.0% (w/w), wherein said salt-sensitive viscosity modulating polymer has a standard emulsion viscosity between 1,700 and 4,500 cPs.
68. The method of any one of paragraphs 65 to 67, wherein said polymer lubricant is carboxymethylcellulose sodium present at a concentration between about 0.01% (w/w) and about 1.0% (w/w).
69. The method of any one of paragraphs 64 to 68, further comprising a compatible solute, wherein said compatible solute is erythritol at a concentration of about 0.25% (w/w) and levocarnitine at a concentration of about 0.25% (w/w).
70. The method of any one of paragraphs 64 to 69, further comprising a tonicity agent, wherein said tonicity agent is glycerin at a concentration between about 0.01% (w/w) and about 5.0% (w/w).
71. The method of any one of paragraphs 44 to 70, further comprising a preservative, wherein said preservative is a stabilize oxychloro compound present at a concentration between about 0.001% (w/w) and about 0.1% (w/w).
72. The method of any one of paragraphs 44 to 71, further comprising a buffer, wherein said buffer is boric acid present at a concentration of about 0.6% (w/w).

73. The method of any one of paragraphs 44 to 72, further comprising a pH adjustment agent, wherein said pH adjustment agent is NaOH.
74. The method of any one of paragraphs 44 to 72, said low salt ophthalmic pharmaceutical composition having pH of about 7.3.
75. The method of paragraph 74, wherein said low salt ophthalmic pharmaceutical composition comprises: castor oil at a concentration between about 0.01% (w/w) and about 10% (w/w); polysorbate 80 at a concentration between about 0.01% (w/w) and about 1.0% (w/w); acrylate/C10-C30 acrylate crosspolymer at a concentration between about 0.01% (w/w) and about 1.0% (w/w), wherein said acrylate/C10-C30 acrylate crosspolymer has a standard emulsion viscosity between 1,700 and 4,500 cPs; carboxymethylcellulose sodium at a concentration between about 0.01% (w/w) and about 1.0% (w/w); glycerin at a concentration between about 0.01% (w/w) and about 5.0% (w/w); a stabilized oxychloro complex preservative at a concentration between about 0.001% (w/w) and about 0.1% (w/w); boric acid at a concentration of about 0.6% (w/w); erythritol at a concentration of about 0.25% (w/w); levocarnitine at a concentration of about 0.25% (w/w); NaOH; and water.
76. The method of paragraph 75, wherein said low salt ophthalmic pharmaceutical composition comprises: castor oil at a concentration of about 0.25% (w/w); polysorbate 80 at a concentration of about 0.5% (w/w); acrylate/C10-C30 acrylate crosspolymer at a concentration of about 0.1% (w/w), wherein said acrylate/C10-C30 acrylate crosspolymer has a standard emulsion viscosity between 1,700 and 4,500 cPs; carboxymethylcellulose sodium at a concentration of about 0.5% (w/w); glycerin at a concentration of about 1.0% (w/w); a stabilized oxychloro complex preservative at a concentration of about 0.01% (w/w); boric acid at a concentration of about 0.6% (w/w); erythritol at a concentration of about 0.25% (w/w); levocarnitine at a concentration of about 0.25% (w/w); NaOH; and water.

DETAILED DESCRIPTION OF THE INVENTION

I. Definitions

Figure 1A:
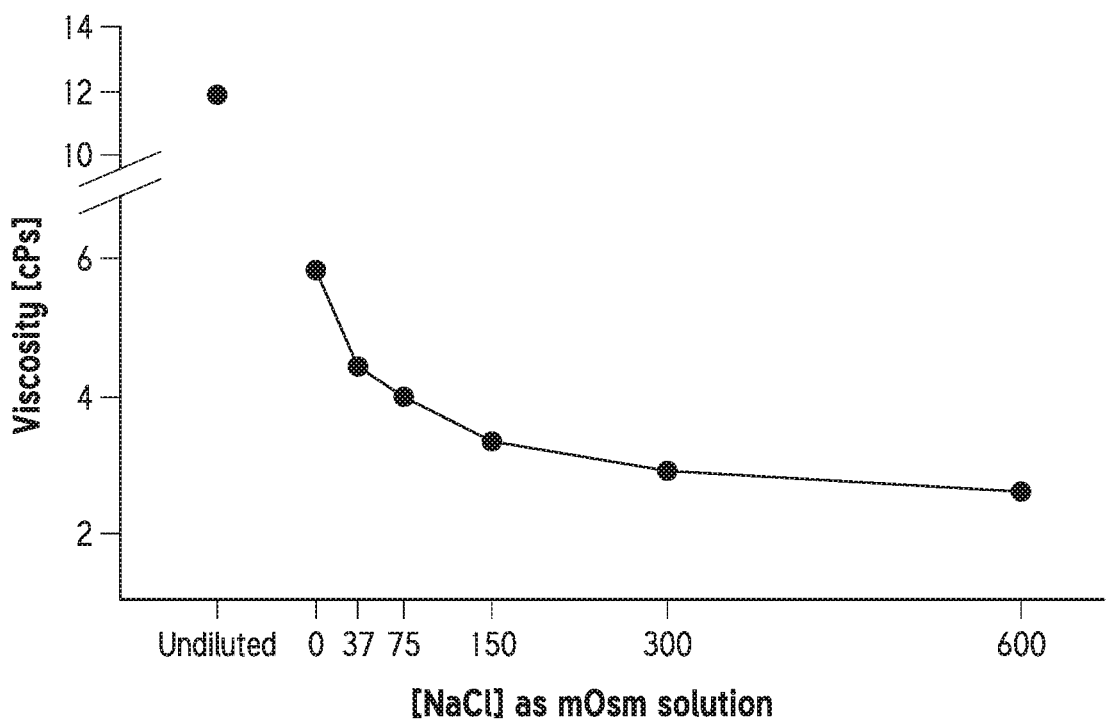
FIG. 1A depicts the dependence of viscosity (cPs) on salt concentration for a low salt ophthalmic pharmaceutical composition disclosed herein. See Example 1.

The term "about" in the context of a numerical value refers, absent express indication otherwise, to the nominal amount±10% thereof.

The terms "clear," "clarity" and the like in the context of ophthalmic pharmaceutical compositions refer to absorbance and/or light scattering (e.g., opacity, pearlescence, and the like) which are sufficiently low such that the ophthalmic pharmaceutical composition appears substantially free of haziness, mistiness or cloudiness to the naked human eye. A clear ophthalmic pharmaceutical composition does not include emulsions that visibly separate into a hydrophobic portion and a hydrophilic portion.

The terms "compatible solute," "osmolytes" and the like in the context of ophthalmic pharmaceutical compositions refers to substances that are taken into the cell and act to counterbalance the osmotic pressure found outside the cell. Without wishing to be bound by any theory, it is believed that compatible solutes have osmoprotective properties which may protect the surface cells of the eye from osmotic stress. It is further believed that the incorporation of compatible solutes increases the clinical usefulness of the composition disclosed herein to contemplate a broader range of subject suffering from dry eye syndrome compared to previous emulsion systems which target lipid deficiency per se or meibomian gland dysfunction.

The terms "dry eye," "dry eye syndrome," "keratitis sicca," "xerophthalmia," "keratoconjunctivitis sicca," and the like refer in the customary sense to a condition or spectrum of conditions wherein the eye is unable to maintain a healthy tear layer (i.e., tear film) sufficient to coat the eye. Dry eye syndrome is more prevalent with age, as subjects typically produce fewer tears with age.

As used herein, the term "effective amount" or "effective dose" refers in the customary sense to an amount which is sufficient to bring about a desired result. Accordingly, a therapeutically effective amount employed in a treatment is a sufficient amount to reduce the extent, undesirable clinical manifestation, of both, of a disease, disorder or condition.

"Formulation," "composition," and "preparation" as used herein are equivalent terms referring to a composition of matter suitable for pharmaceutical use (i.e., producing a therapeutic effect as well as possessing acceptable pharmacokinetic and toxicological properties).

The term "low salt" as used herein in the context of an ophthalmic pharmaceutical composition refers to a salt content which is sufficiently low so as to provide a stabilized sub-micron emulsion within the ophthalmic pharmaceutical composition. Salt content can be measured by a variety of methods known in the art, e.g., measurement of ionic strength. Accordingly, the term "low salt ophthalmic pharmaceutical composition" refers to a pharmaceutical composition for use in the eye having sufficiently low salt content that a sub-micro emulsion which includes a surfactant and a therapeutic lipid is stable therein.

The term "polymer lubricant" refers to a polymeric agent able coat the ocular surface (i.e., demulcent) and provide lubrication to the eye. Exemplary polymer lubricants useful in the composition and methods disclosed herein include any of a variety of cellulose derivatives, e.g., hydroxymethyl cellulose, hydroxyethyl cellulose, carboxymethyl cellulose and the like, polyvinyl pyrrolidone, polyvinyl alcohol, and the like, and mixtures thereof.

The term "prevent" as used herein refers to a decrease in the occurrence of dermatological symptoms (e.g., urticarial wheals) in a patient. The prevention may be complete (i.e., no detectable symptoms) or partial, so that fewer symptoms are observed than would likely occur absent treatment.

As used herein, the terms "prevent" and "treat" are not intended to be absolute terms. Treatment can refer to any delay in onset, e.g., reduction in the frequency or severity of symptoms, amelioration of symptoms, improvement in patient comfort, reduction in symptoms of dry eye, and the like. The effect of treatment can be compared to an individual or pool of individuals not receiving a given treatment, or to the same patient before, or after cessation of, treatment.

The terms "salt-sensitive viscosity modulating polymer," "salt-sensitive polymer" and the like refer to polymeric agents useful to maintain a stable sub-micron emulsion under low salt conditions within a low salt ophthalmic pharmaceutical composition disclosed herein, and which in turn destabilize, upon an increase in salt content, the sub-micron emulsion. The term "destabilize" in this context refers to a change in the sub-micron emulsion such that therapeutic lipid is released from the sub-micron emulsion. Accordingly, the terms "salt-sensitive" and the like in this context refer to a change in one or more properties of a compound (e.g., conformation, extent of hydration, effective charge due to ion screening, viscosity and the like) in response to a change in salt concentration. Exemplary salt-sensitive viscosity modulating polymers include polymers of acrylic acid which are crosslinked with polyalkenyl ethers or divinyl glycol. A preferred salt-sensitive viscosity modulating polymer includes crosslinked copolymers of acrylic acid and $C_{10}$-$C_{30}$ alkyl acrylate, commonly referred to as Pemulen™ TR-2 (Lubrizol Corporation, Wickliffe, Ohio).

The term "sorbitan ester" in the context of surfactants refers in the customary sense to a class of polyethylene glycol (i.e., PEG) derivatives of sorbitan which are further esterified with fatty acids, as known in the art.

The term "standard emulsion viscosity" as used herein refers to the experimentally determined viscosity of a 0.2% solution of salt-sensitive viscosity modulating polymer as measured in a standardized procedure according to manufacturer's recommendation. See e.g., Lubrizol Test Procedure SA-015, Ed: August 2003, Lubrizol Advanced Materials, Inc., Cleveland, Ohio.

The term "sub-micron emulsion" refers to an emulsion containing components having an extent in the longest dimension of less than about 1 micron. "Emulsion" refers in the customary sense to a mixture of two or more immiscible liquid components, one component (e.g., a therapeutic lipid described herein or mixture thereof including surfactant) being dispersed through the other component (e.g., the aqueous component of a composition described herein).

The term "surfactant" refers in the customary sense to compounds able to lower the surface tension of liquid, the interfacial tension between two liquids, or the surface tension between a liquid and a solid.

Unless indicated otherwise, the term "tear" as used herein refers in the customary sense to the basal tears of the mammalian eye which function to continuously bathe and nourish the cornea. Other types of tear include reflex tears resulting e.g., from irritation of the eye by foreign particles or lacrimator compounds, and psychic tears resulting, e.g., from strong emotional stress, anguish, or physical pain.

The terms "tear film," "precorneal film" and like refer in the customary sense to the multilayered coating of the normal eye which includes an innermost mucous layer, a middle aqueous layer, and an outermost lipid layer. The innermost mucous layer contains proteins, e.g., mucin produced by the goblet cells of the conjunctiva, and facilitates even spreading of the overlying middle aqueous layer, e.g., by providing a hydrophilic layer coating the cornea. The middle aqueous layer is produced by the lacrimal glands and includes water, proteins and salt as known in the art. The outermost lipid layer contains oils produced by the meibomian glands and coats the middle aqueous layer, providing a hydrophobic barrier that envelopes tears and prevents outflow, e.g., to the cheek. Importantly, the outermost lipid layer decreases evaporation of the middle aqueous layer.

The term "therapeutic lipid" refers to a pharmaceutically acceptable amphiphilic or hydrophobic agent which acts to supplement and/or enhance the naturally occurring oils produced by the meibomian glands which form the outermost lipid layer of the tear film. In some embodiments, the therapeutic lipid is a hydrophobic agent. Without wishing to be bound by any theory, it is believed that symptoms of dry eye syndrome can result from insufficient production of naturally occurring oils produced by the meibomian glands. Accordingly, it is further believed that supplement and/or enhancement by a therapeutic lipid described herein is beneficial to the treatment of dry eye syndrome.

The term "therapeutically effective amount" as used herein refers to that amount of the composition or agent in a composition sufficient to ameliorate one or more aspects of the disorder.

Therapeutic efficacy can also be expressed as "-fold" increase or decrease. For example, a therapeutically effective amount can have at least a 1.2-fold, 1.5-fold, 2-fold, 5-fold, or more effect over a control.

The term "tonicity agent" as used herein refers in the customary sense to a compound which can modulate the effective osmotic pressure within a cell. For example, for comfort during administration or instillation, the tonicity of pharmaceutical dosage forms can be adjusted by a tonicity agent. Exemplary tonicity agents include dextrose, glycerin, mannitol, KCl, and NaCl. Tonicity agents can provide additional benefit, including e.g., function as a humectant or lubricant.

The term "treatment" as used herein refers to an approach (e.g., a procedure or regimen) for obtaining beneficial or desired results, including clinical results. "Treating," "palliating," or "ameliorating" a disease, disorder or condition means that the extent, undesirable clinical manifestations, or both, of a disease, disorder or condition are lessened and/or the time course of the progression is slowed (i.e., lengthened in time), as compared to not treating the disease, disorder or condition. For purposes of the methods disclosed herein, beneficial or desired clinical results include, but are not limited to, alleviation or amelioration of one or more symptoms (e.g., symptoms of dry eye syndrome), diminishment of extent of disorder, stabilized (i.e., not worsening) state of disorder, delay or slowing of disorder progression, amelioration or palliation of the disorder, and remission (whether partial or total), whether detectable or undetectable.

"Treating" and "treatment" as used herein may include prophylactic treatment. Treatment methods include administering to a subject a therapeutically effective amount of an active agent. The administering step may consist of a single administration or may include a series of administrations. The length of the treatment period depends on a variety of factors, such as the severity of the condition, the age of the patient, the concentration of active agent, the activity of the compositions used in the treatment, or a combination thereof. It will also be appreciated that the effective dosage of an agent used for the treatment or prophylaxis may increase or decrease over the course of a particular treatment or prophylaxis regime. Changes in dosage may result and become apparent by standard diagnostic assays known in the art. In some instances, chronic administration may be required. For example, the compositions are administered to the subject in an amount and for a duration sufficient to treat the patient.

Delivering lipids to the human tear film to supplement and enhance the native lipid layer, often deficient due to dysfunction of meibomian glands and other causes, is a recognized strategy in treating signs and symptoms of dry eye. This is in theory especially beneficial in low humidity or when other internal/external factors increase tear film evaporation. Excessive loss of water from the tear film causes an increase in salt content and causes hyperosmotic stress to the cells of the ocular surface.

The native lipid layer is very thin and the total volume of lipid is a small fraction of the total tear film volume. To enhance the structure and function of the lipid layer by topical application of a lipid-containing drop requires only a small volume of oil to be delivered; excess lipid will displace and disrupt the total aqueous volume, by far the greatest component of tears. It is also necessary that the lipid be delivered quickly, during the brief contact time of a topical eye drop. Finally, the lipid delivered needs to become established as part of the native lipid layer, at the air interface.

The challenge of lipid release from an emulsion has been approached by using substantial amounts of lipid (1-5%) and/or building an emulsion system that readily separates. The disadvantage of this approach includes: the product requires shaking, the clarity of the emulsion is greatly reduced, the total volume of lipid delivered to the eye is potentially large and variable and tolerability can be lower than a fully aqueous eye drop.

An alternate means of lipid release involves the use of a salt-sensitive emulsion system in a product intended for topical use that is largely free of salt. This system uses a surfactant and viscosity-increasing polymer to hold the lipid (eg. castor oil) in a stable sub-micron emulsion. When mixed with human tear, the natural salt content (often further elevated in dry eye) is sufficient to rapidly cause a drop-in product viscosity due to action on the polymer structure. This loss of viscosity allows lipid release to occur to a significantly greater degree and much faster.

Efficiency of lipid delivery can be defined as the amount of lipid released from the emulsion, as a proportion of total lipid content, over time under standard test conditions.

Efficiency of lipid delivery in the presence of salt is supported, for example, using simple laboratory methods. Specifically, when diluted with water, this system shows a loss of viscosity proportional to water volume added. When exposed to salt (NaCl) by mixing 1:1 with even a weak saline solution (30 mOsm) a loss of viscosity of over 60% occurs vs. 50% when mixed with water. Higher saline strength (up to about 600 mOsm) caused significantly greater loss of viscosity, confirming action of salt on polymer structure.

The release of lipid was demonstrated using a controlled centrifuge with real-time integrated optical detector (Lumisizer). During 2 minutes of 4000 RPM stress, uniformity of the emulsion was confirmed by equivalent optical transmission from bottom to top of the centrifuge sample holder for both full strength and water-diluted product. However, diluting the product with saline (volume and concentration replicating on-eye use) showed a clear and remarkable change in product uniformity consistent with lipid release and migration to the top of the sample holder, consistent with "floating" to the air interface. Surprisingly and beneficially, this may occur without coalescence (no increase in average lipid droplet size) allowing the lipid to mix into the native layer more effectively. Average particle (lipid droplet size) was unchanged when saline was added (Horiba).

Clinical results have confirmed that the new lipid emulsion system works effectively in prolonging TBUT (tear break-up time) yet demonstrates tolerability and comfort improvements vs. an emulsion more optimized for drug delivery.

The benefits of using a salt-sensitive emulsion system as shown in the Tables, that is largely free of salts, include but are not limited to:
1) No need to shake the product—excellent in bottle stability and uniformity;
2) Efficient delivery of lipid on eye due to the salt-induced decrease in viscosity and destabilization of emulsion structure enabling more efficient lipid release;
3) Improved tolerability by lowering total lipid content;
4) Effective stabilization and supplementation of the native lipid layer; and
5) Possibly greater delivery of beneficial lipid in patients with higher tear salt content, a so-called "smart" vehicle.

The incorporation of osmoprotectants (1-carnitine and erythritol) and humectants/lubricants (glycerin and carboxymethylcellulose increases the clinical usefulness of this product to a broader range of dry eye patients than other emulsion systems targeting lipid deficiency or meibomian gland dysfunction.

II. Design Rationale

The salt-sensitive viscosity modulating polymers contemplated in the practice of the compositions and methods disclosed herein undergo a salt-sensitive change in physical properties (e.g., change in viscosity) upon a change in salt concentration in the milieu of a sub-micron emulsion containing the polymers. Specifically, upon an increase in salt concentration, the sub-micron emulsions undergo a decrease in viscosity. Without wishing to be bound by any theory, it is believed that such a decrease in viscosity is associated with a destabilization of the sub-micron emulsion leading to separation of the lipid phase (e.g., therapeutic lipid) from associated surfactant, which therapeutic lipid then becomes available to exert a therapeutic benefit in the supplementation and enhancement of the outer lipid layer of the tear film.

Traditionally, ionic or non-ionic surfactants stabilize oil-in-water emulsions by the formation of lamellar liquid crystalline layers at the emulsion interface to afford micelles, as known in the art. However, as further known in the art, such traditional methods of emulsification require relatively high levels (e.g., 3-7%) of surfactant. Without wishing to be bound by any theory, it is believed that the salt-sensitive viscosity modulating polymers contemplated herein increase the stability of oil-in-water emulsions under low salt conditions by thickening and adding structure to the water phase, resulting in an aqueous gel around each oil droplet. Thus, incorporation of salt-sensitive viscosity modulating polymers reduces the requirement for relatively high levels of surfactant in order to achieve stable emulsification. It is further believed that the hydrophobic portions of the salt-sensitive viscosity modulating polymers associate with the oil droplet. Thus, when two emulsified oil droplets approach each other, a physical repulsive force is generated by the presence of the adsorbed gel layers. Accordingly, the oil droplets do not associate with each other and remain in a stable sub-micron emulsion. Moreover, by decreasing the total therapeutic lipid content of the composition, it is believed that the compositions disclosed herein provide improved tolerability in the clinic.

As known in the art, tears (i.e., basal tears) have about the same osmolality as the internal fluids of the body, equivalent to about 0.9% NaCl (i.e., about 150 mM). Moreover, without wishing to be bound by any theory, it is believed that in dry eye syndrome, the middle aqueous layer of the tear film can undergo evaporation leading to increased local salt concentration at the eye. Thus, it has been found that application of a composition disclosed herein to the eye can result in destabilization of the sub-micron emulsion of the composition due to the increased salt content at the eye, thereby providing therapeutic lipid beneficial at the surface of the eye. Moreover, without wishing to be bound by any theory, it is believed that higher salt content of the nascent tear film and underlying corneal surface found in dry eye syndrome can result in greater delivery of therapeutic lipid, due to more effective destabilization of the sub-micron emulsion and release of therapeutic lipid.

Moreover, it has been surprisingly found that a further benefit of the compositions disclosed herein is a lack of coalescence of the therapeutic lipid upon instillation in the eye, resulting in no increase in lipid droplet size. Accordingly, the lipid can mix more effectively into the native tear film.

III. Compositions

In a first aspect, there is provided a low salt ophthalmic pharmaceutical composition which includes a sub-micron emulsion, a polymer lubricant, and a salt-sensitive viscosity modulating polymer. The sub-micron emulsion includes a surfactant and a therapeutic lipid.

In one embodiment, the low salt ophthalmic pharmaceutical composition is clear. In one embodiment, the composition has approximately the same clarity as pure water (e.g. upon inspection with the naked human eye). Thus, in some embodiments, the composition scatters sufficiently low levels of visible light that the composition appears clear to the eye. In one embodiment, the composition is effectively clear. The term "effectively clear" refers to a small amount of absorbance and/or light scattering which nonetheless allows light to transit the composition without appreciable blurring and/or distortion. In some embodiments, the clear low salt ophthalmic pharmaceutical composition allows transmission of at least about 20% T of visible light. In some embodiments, the clear low salt ophthalmic pharmaceutical composition allows transmission of at least about 25% T of visible light. In some embodiments, the clear low salt ophthalmic pharmaceutical composition allows transmission of at least about 30% T of visible light. In some embodiments, the clear low salt ophthalmic pharmaceutical composition allows transmission of at least about 35% T of visible light. In some embodiments, the clear low salt ophthalmic pharmaceutical composition allows transmission of at least about 40% T of visible light. In some embodiments, the clear low salt ophthalmic pharmaceutical composition allows transmission of at least about 45% T of visible light. In some embodiments, the clear low salt ophthalmic pharmaceutical composition allows transmission of at least about 50% T of visible light. In some embodiments, the clear low salt ophthalmic pharmaceutical composition allows transmission of at least 55% T of visible light. In some embodiments, the clear low salt ophthalmic pharmaceutical composition allows transmission of at least 60% T of visible light. In some embodiments, the clear low salt ophthalmic pharmaceutical composition allows transmission of at least 65% T of visible light. In some embodiments, the clear low salt ophthalmic pharmaceutical composition allows transmission of at least 70% T of visible light. In some embodiments, the clear low salt ophthalmic pharmaceutical composition allows transmission of at least 75% T of visible light. In some embodiments, the clear low salt ophthalmic pharmaceutical composition allows transmission of at least 80% T of visible light. Absent an indication otherwise, "% T" refers to percentage transmission of light using a path length of 1 cm.

Further to any embodiment disclosed herein, in one embodiment the therapeutic lipid is a fatty acid glyceride. In one embodiment, the fatty acid glyceride is a castor oil, olive oil, peanut oil, corn oil, or sunflower oil.

In one embodiment, the therapeutic lipid is castor oil. In one embodiments, the castor oil is present at a concentration between about 0.01% (w/w) and about 10% (w/w). In one embodiment, the castor oil is present at a concentration of about 0.25% (w/w).

In one embodiment, the composition includes a plurality of therapeutic lipids. For example, in one embodiment the therapeutic lipid is a first therapeutic lipid, and the low salt ophthalmic pharmaceutical composition further includes a second therapeutic lipid. In one embodiment, the composition further includes a third therapeutic lipid. In one embodiment, the composition further includes a fourth therapeutic lipid, in one embodiment, the composition further includes a fifth therapeutic lipid. Further to each embodiment contemplating a plurality of therapeutic lipids, the first, second, third, fourth and fifth therapeutic lipids are each different and if present are castor oil, olive oil, peanut oil, corn oil, or sunflower oil.

Further to any embodiment including a plurality of therapeutic lipids, in one embodiment the plurality of therapeutic lipids are present at a total concentration between about 0.01% (w/w) and about 10% (w/w). In one embodiment, the plurality of therapeutics lipids are present at a concentration of about 0.25% (w/w).

In one embodiment, the surfactant within the low salt ophthalmic pharmaceutical composition is a sorbitan ester. Exemplary surfactants contemplated for use in the compositions and methods disclosed herein include polysorbate 20 (i.e., primarily polyoxyethylene [20] sorbitan monolaurate), polysorbate 40 (i.e., primarily polyoxyethylene [20] sorbitan monopalmitate), polysorbate 60 (i.e., primarily polyoxyethylene [20] sorbitan monostearate), or polysorbate 80 (i.e., polyoxyethylene [20] sorbitan monooleate).

In one embodiment, the surfactant is polysorbate 80. In one embodiment, polysorbate 80 is present at a concentration between about 0.01% (w/w) and about 1.0% (w/w). In one embodiment, polysorbate 80 is present at a concentration of about 0.5% (w/w).

In one embodiment, the salt-sensitive viscosity modulating polymer of the low salt ophthalmic pharmaceutical composition is an acrylate/$C_{10}$-$C_{30}$ acrylate crosspolymer. In one embodiment, the salt-sensitive viscosity modulating polymer has a standard emulsion viscosity between 1,700 and 4,500 cPs. A useful commercially available acrylate/$C_{10}$-$C_{30}$ acrylate crosspolymer is known as Pemulen™ TR-2 (Lubrizol Corporation, Wickliffe, Ohio).

In one embodiment, the salt-sensitive viscosity modulating polymer of the low salt ophthalmic pharmaceutical composition is present at a concentration between about 0.01% (w/w) and about 1.0% (w/w). In one embodiment, the salt-sensitive viscosity modulating polymer is present at a concentration of about 0.1% (w/w).

Further to any embodiment described above, in one embodiment of the low salt ophthalmic pharmaceutical composition is a demulcent.

Further to any embodiment described above, in one embodiment the polymer lubricant is a carboxymethylcellulose lubricant. As customarily used in the art, the terms "carboxymethylcellulose," "cellulose gum," "CMC" and the like refer to cellulose derivatives having carboxymethyl (i.e., —CH$_2$—COOH) groups substituted at some of the pendant hydroxyl moieties of the polymerized D-glucose units forming the linear chain of the cellulose. Cellulose chain length and the degree of carboxymethylation can be optimized to afford specific properties, including viscosity modulation (i.e., thickening) and stabilization of emulsions. Accordingly, the term "carboxymethylcellulose lubricant" refers to a composition including one or more carboxymethylcelluloses having specific chain lengths and degrees of carboxymethylation.

In one embodiment, the polymer lubricant is carboxymethylcellulose sodium, preferably carboxymethylcellulose sodium (low viscosity, 7LFPH). In one embodiment, the carboxymethylcellulose sodium is present at a concentration between about 0.01% (w/w) and about 1.0% (w/w). In one embodiment, the carboxymethylcellulose sodium is present at a concentration of about 0.5% (w/w).

Further to any embodiment described above, in one embodiment the low salt ophthalmic pharmaceutical composition further includes one or more compatible solutes. Exemplary compatible solutes include polyols and zwitterionic amino acids. In one embodiment, the compatible solute is a polyol. In one embodiment, the compatible solute is a zwitterionic amino acid. In one embodiment, the compatible solute includes polyols and zwitterionic amino acids. In one embodiment, the compatible solute includes a polyol and a zwitterionic amino acid.

In one embodiment, the low salt ophthalmic pharmaceutical composition includes erythritol or levocarnitine. In one embodiment, erythritol is present at a concentration between about 0.01% (w/w) and about 1.0% (w/w). In one embodiment, levocarnitine is present at a concentration between about 0.01% (w/w) and about 1.0% (w/w). In one embodiment, erythritol is present at a concentration of about 0.25% (w/w). In one embodiment, levocarnitine is present at a concentration of about 0.25% (w/w). In one embodiment, erythritol is present at a concentration of about 0.25% (w/w), and levocarnitine is present at a concentration of about 0.25% (w/w).

Further to any embodiment described above, in one embodiment the low salt ophthalmic pharmaceutical composition further includes one or more tonicity agents. It is understood that a tonicity agent, e.g., glycerin, can also function as a demulcent. Thus, in one embodiment the tonicity of the low salt ophthalmic pharmaceutical composition is a demulcent.

In one embodiment, the tonicity agents of the low salt ophthalmic pharmaceutical composition is glycerin present at a concentration between about 0.01% (w/w) and about 5.0% (w/w). In one embodiment, glycerin is present at a concentration of about 1.0% (w/w).

Further to any embodiment described above, in one embodiment the low salt ophthalmic pharmaceutical composition further includes a preservative. Exemplary preservatives employed in topic ophthalmic pharmaceutical compositions include quaternary ammonium (e.g., benzalkonium chloride, polyquaternium-1, and the like), mercurials (e.g., thimerosal), alcohols (e.g., chlorobutanol, benzyl alcohol, and the like), carboxylic acids (e.g., sorbic acid and the like), phenols (methyl or propyl parabens), amidines (e.g., chlorhexidine), and other compounds (e.g., stabilized oxychloro complex). An exemplary stabilized oxychloro complex is Purite® (Purite Ltd, Oxon, UK).

In one embodiment, the low salt ophthalmic pharmaceutical composition includes a stabilized oxychloro complex. In one embodiment, the stabilized oxychloro complex is present at a concentration between about 0.001% (w/w) and about 0.1% (w/w). In one embodiment, the stabilized oxychloro complex is present at a concentration of about 0.01% (w/w).

Further to any embodiment described above, in one embodiment the low salt ophthalmic pharmaceutical composition further includes a buffer. Exemplary buffers useful in the compositions disclosed herein include inorganic acids (e.g., borate, phosphate, and the like), organic acids (e.g., lower alkyl carboxylic acids), and amines including primary, secondary, tertiary and quaternary amines as known in the art. The term "lower alkyl carboxylic acid" refers to $C_1$-$C_6$ alkyl having at least one —COOH substituent.

In one embodiment of the low salt ophthalmic pharmaceutical composition, the buffer is boric acid present at a concentration between about 0.01% (w/w) and about 1.0% (w/w). In one embodiment, boric acid is present at a concentration of about 0.6% (w/w).

Further to any embodiment described above, in one embodiment the low salt ophthalmic pharmaceutical composition further includes a pH adjustment agent. Exemplary pH adjustment agents include strong acids (e.g., HCl) and strong bases (e.g., NaOH). In one embodiment, the pH adjustment agent is NaOH. In one embodiment, the pH of the low salt ophthalmic pharmaceutical composition is in the range of about pH 7 to pH 8. In one embodiment, the pH of the low salt ophthalmic pharmaceutical composition is about pH 7.3.

Further to any embodiment described above, in one embodiment low salt ophthalmic pharmaceutical composition includes castor oil at a concentration between about 0.01% (w/w) and about 10% (w/w); polysorbate 80 at a concentration between about 0.01% (w/w) and about 1.0% (w/w); acrylate/C10-C30 acrylate crosspolymer at a concentration between about 0.01% (w/w) and about 1.0% (w/w), wherein said acrylate/C10-C30 acrylate crosspolymer has a standard emulsion viscosity between 1,700 and 4,500 cPs; carboxymethylcellulose sodium at a concentration between about 0.01% (w/w) and about 1.0% (w/w); glycerin at a concentration between about 0.01% (w/w) and about 5.0% (w/w); a stabilized oxychloro complex preservative at a concentration between about 0.001% (w/w) and about 0.1% (w/w); boric acid at a concentration of about 0.6% (w/w); erythritol at a concentration of about 0.25% (w/w); levocarnitine at a concentration of about 0.25% (w/w); NaOH; and water. See Table III. With reference to Tables I and II and III, the term "q.s." refers in the customary sense to a sufficient amount to afford the nominal amount or pH.

TABLE II

Range of components of low salt ophthalmic pharmaceutical composition.

| Component | Range of Approximate Amounts | Units | Function |
| --- | --- | --- | --- |
| Polysorbate 80 | 0.01 to 1.0 | % (w/w) | Surfactant |
| Carboxymethyl cellulose sodium | 0.01 to 1.0 | % (w/w) | Polymer lubricant |
| Glycerin | 0.01 to 5.0 | % (w/w) | Tonicity agent |
| stabilized oxychloro complex | 0.001 to 0.1 | % (w/w) | Preservative |
| Boric acid | 0.6 | % (w/w) | Buffer |

TABLE II-continued

Range of components of low salt ophthalmic pharmaceutical composition.

| Component | Range of Approximate Amounts | Units | Function |
|---|---|---|---|
| Acrylate/$C_{10}$-$C_{30}$ acrylate crosspolymer (Pemulen ™ TR-2) | 0.01 to 1.0 | % (w/w) | Salt-sensitive viscosity modulating polymer |
| Castor oil | 0.01 to 10 | % (w/w) | Therapeutic lipid |
| Erythritol | 0.25 | % (w/w) | Compatible solute |
| Levocarnitine | 0.25 | % (w/w) | Compatible solute |
| NaOH | q.s. to pH 7.3 | pH | QS Adjustment |
| Water for injection | q.s. to 100% | % (w/w) | QS Adjustment |

In one embodiment, the low salt ophthalmic pharmaceutical composition has a formulation as set forth in Table III following.

TABLE III

Exemplary low salt ophthalmic pharmaceutical composition.

| Component | Range of Approximate Amounts | Units | Function |
|---|---|---|---|
| Polysorbate 80 | 0.5 | % (w/w) | Surfactant |
| Carboxymethyl cellulose sodium | 0.5 | % (w/w) | Polymer lubricant |
| Glycerin | 1.0 | % (w/w) | Tonicity agent |
| stabilized oxychloro complex | 0.01 | % (w/w) | Preservative |
| Boric acid | 0.6 | % (w/w) | Buffer |
| Acrylate/$C_{10}$-$C_{30}$ acrylate crosspolymer (Pemulen ™ TR-2) | 0.1 | % (w/w) | Salt-sensitive viscosity modulating polymer |
| Castor oil | 0.25 | % (w/w) | Therapeutic lipid |
| Erythritol | 0.25 | % (w/w) | Compatible solute |
| Levocarnitine | 0.25 | % (w/w) | Compatible solute |
| NaOH | q.s. to pH 7.3 | pH | QS Adjustment |
| Water for injection | q.s. to 100% | % (w/w) | QS Adjustment |

IV. Methods of Use

In another aspect, there is provided a method for treating dry eye syndrome. The method includes administering to a subject in need of treatment of dry eye syndrome a therapeutically effective amount of a low salt ophthalmic pharmaceutical composition as disclosed herein, thereby treating dry eye syndrome in the subject. In one embodiment, the low salt ophthalmic pharmaceutical composition includes a sub-micron emulsion, a polymer lubricant, and a salt-sensitive viscosity modulating polymer, as disclosed herein, wherein the sub-micron emulsion includes a surfactant and a therapeutic lipid.

In one embodiment, the therapeutic lipid within the low salt ophthalmic pharmaceutical composition is castor oil at a concentration between about 0.01% (w/w) and about 10% (w/w).

In one embodiment, the surfactant is polysorbate 80 at a concentration between about 0.01% (w/w) and about 1.0% (w/w).

In one embodiment, the salt-sensitive viscosity modulating polymer includes acrylate/C10-C30 acrylate crosspolymer present at a concentration between about 0.01% (w/w) and about 1.0% (w/w). In one embodiment, the salt-sensitive viscosity modulating polymer has a standard emulsion viscosity between 1,700 and 4,500 cPs.

In one embodiment, the polymer lubricant is carboxymethylcellulose sodium present at a concentration between about 0.01% (w/w) and about 1.0% (w/w).

In one embodiment, the low salt ophthalmic pharmaceutical composition further includes a compatible solute. In one embodiment, the compatible solute is erythritol at a concentration of about 0.25% (w/w) and levocarnitine at a concentration of about 0.25% (w/w).

In one embodiment, the low salt ophthalmic pharmaceutical composition further includes a tonicity agent. In one embodiment, the tonicity agent is glycerin at a concentration between about 0.01% (w/w) and about 5.0% (w/w).

In one embodiment, the low salt ophthalmic pharmaceutical composition further includes a preservative. In one embodiment, the preservative is a stabilize oxychloro compound present at a concentration between about 0.001% (w/w) and about 0.1% (w/w).

In one embodiment, the low salt ophthalmic pharmaceutical composition further includes a buffer. In one embodiment, the buffer is boric acid present at a concentration of about 0.6% (w/w).

In one embodiment, the low salt ophthalmic pharmaceutical composition further includes a pH adjustment agent. In one embodiment, the pH adjustment agent is NaOH.

In one embodiment, the low salt ophthalmic pharmaceutical composition has a pH of about 7.3.

In one embodiment, the low salt ophthalmic pharmaceutical composition includes the components as set forth in Table 1. In one embodiment, the low salt ophthalmic pharmaceutical composition includes the components as set forth in Table II.

V. Examples

Example 1. Effect of Dilution on Viscosity With and Without Salt

A low salt ophthalmic pharmaceutical composition was formulated to deliver therapeutic lipid and lubricating polymers to the precorneal tear fluid. A salt-sensitive viscosity modulating polymer, as disclosed herein, was used to stabilize the lipid in solution yet allow efficient lipid delivery on the eye when mixed with salts in the tear film upon instillation. Delivery of therapeutic lipid to the lipid layer of the tear film was modeled by diluting the low salt ophthalmic pharmaceutical composition with a salt solution and measuring the associated change in viscosity and lipid distribution. As control, the results were compared with a marketed emulsion eye drop lacking salt-sensitive viscosity modulating polymer. The term "sample" in this section refers to a low salt ophthalmic pharmaceutical composition as set forth in Table 2 above. The term "control" refers to a marketed emulsion eye drop lacking salt-sensitive viscosity modulating polymer.

Methods. Viscosity change measurements employed a Brookfield viscometer (25° C., spindle 18, 30 rpm) (Brookfield Engineering laboratories, Middleboro, Mass.), before and after dilution of sample 1:1 with water or salt solution ranging from 30 to 600 mOsm NaCl.

Viscosity measurements were repeated with concentrated NaCl to confirm initial results.

Results. As depicted in FIG. 1A, the viscosity of the tested sample decreased monotonically as a function of salt concentration. When diluted 1:1 with water, the viscosity of the sample was reduced by about 51%. When diluted 1:1 with 30 to 600 mOsm NaCl, the viscosity loss was 62.7% to 78.0%.

In contrast, the control composition displayed equivalent reduction in viscosity upon dilution with either water to salt solution.

Figure 1B:
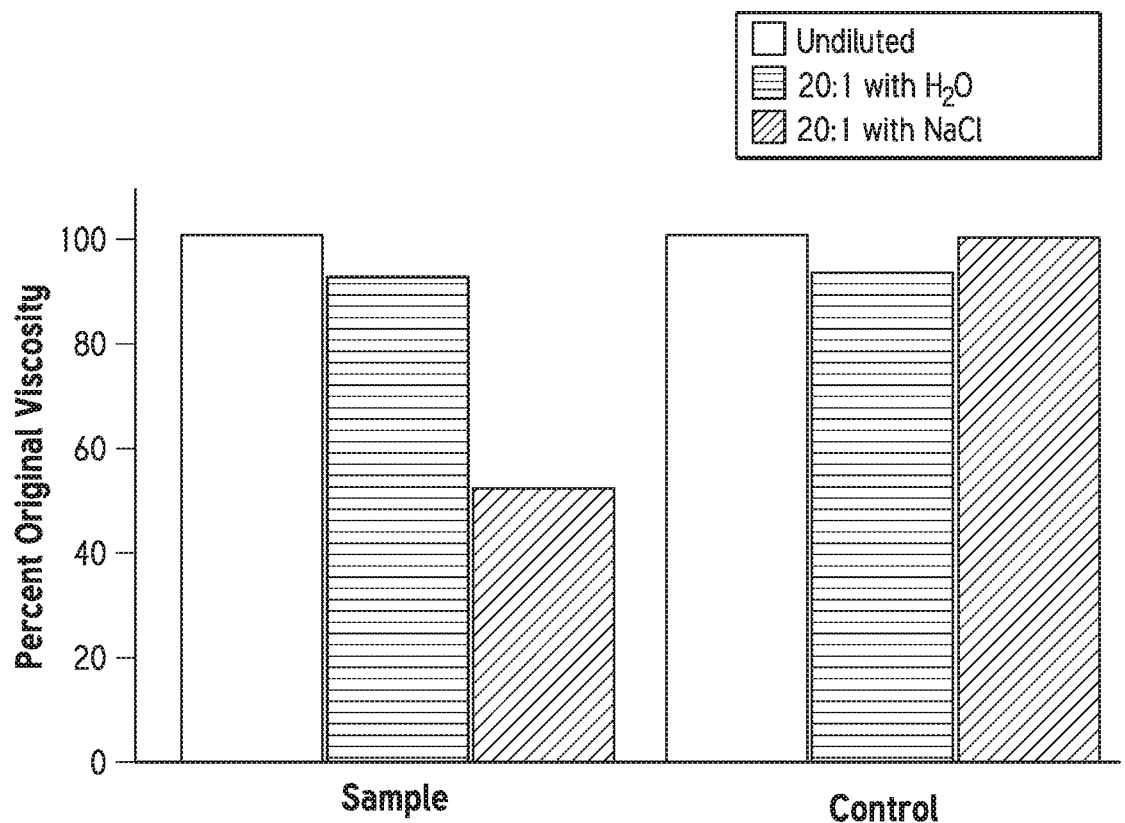
FIG. 1B depicts a histogram of percent change in viscosity upon dilution with water and salt for the sample and control described in Example 1. Legend (left to right): undiluted (open); diluted 20:1 with water (horizontal stripes); diluted 20:1 with 9% NaCl (diagonal stripes).

As shown in FIG. 1B, dilution of the sample of low salt ophthalmic pharmaceutical composition at 20:1 with water or 9% NaCl afforded a percent change reduction in viscosity of about 9% or about 49%, respectively. In contrast, dilution of the control eye drop composition resulted in a percent change reduction in viscosity of about 8% and 1%, respectively, for dilution 20:1 with water and 9% NaCl.

Summary. The viscosity reduction upon increased salt concentration in a sample low salt ophthalmic pharmaceutical composition was greater than observed for the control eye drop lacking salt-sensitive viscosity modulating polymer. The greatest viscosity difference for the sample was observed between dilution with water and dilution with 37 mOsm NaCl. In contrast, the viscosity of the control was observed to correlate only with dilution and not with salt concentration.

Example 2. Effect of Stability of Water and Salt Concentration

Introduction. The stability and uniformity of the emulsions described in Example 1 was investigated under undiluted and diluted conditions.

Methods. Assessment of stability and uniformity of sample compositions employed a time-controlled centrifuge with integrated optical detector (Lumisizer®, L.U.M. GmbH, Berlin, Germany). Samples were undiluted, or diluted 1:20 with water or concentrated (9%) NaCl resulting in a final concentration of 0.45% NaCl simulating the saline concentration of a drop of ophthalmic pharmaceutical composition on the tear film. Concentrated NaCl was used to minimize the dilution effect on light transmittance. Scans were taken repetitively for 2-min at 4000 rpm.

Figure 2A:
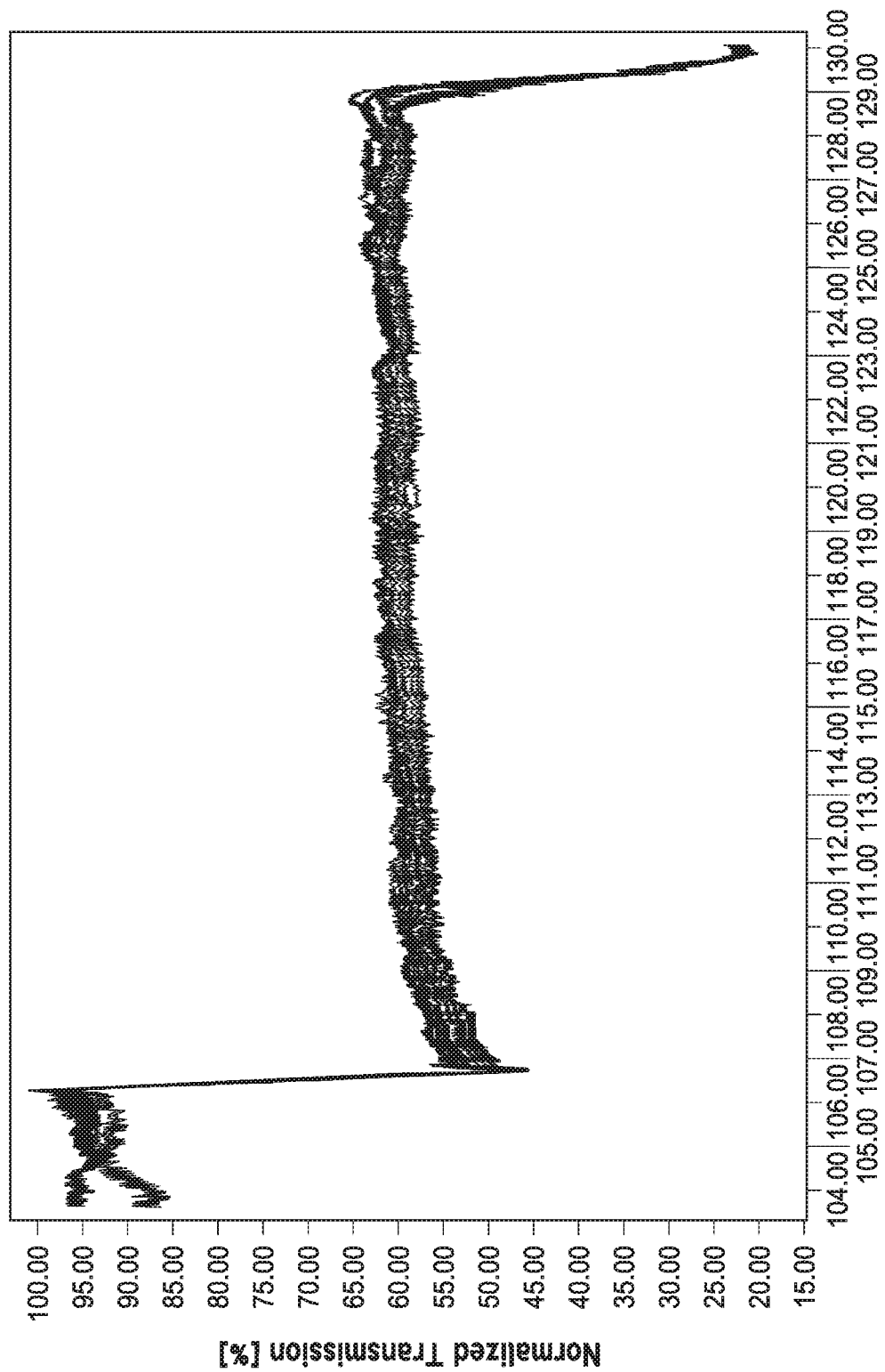
FIGS. 2A-2B depict overlaid real-time integrated optical detector scans in a time-controlled centrifuge of undiluted sample (FIG. 2A) and control (FIG. 2B) as described in Example 2. Legend: X-axis: position (mm) along the centrifugal chamber; Y-axis: light transmissions (% T).
Figure 2B:
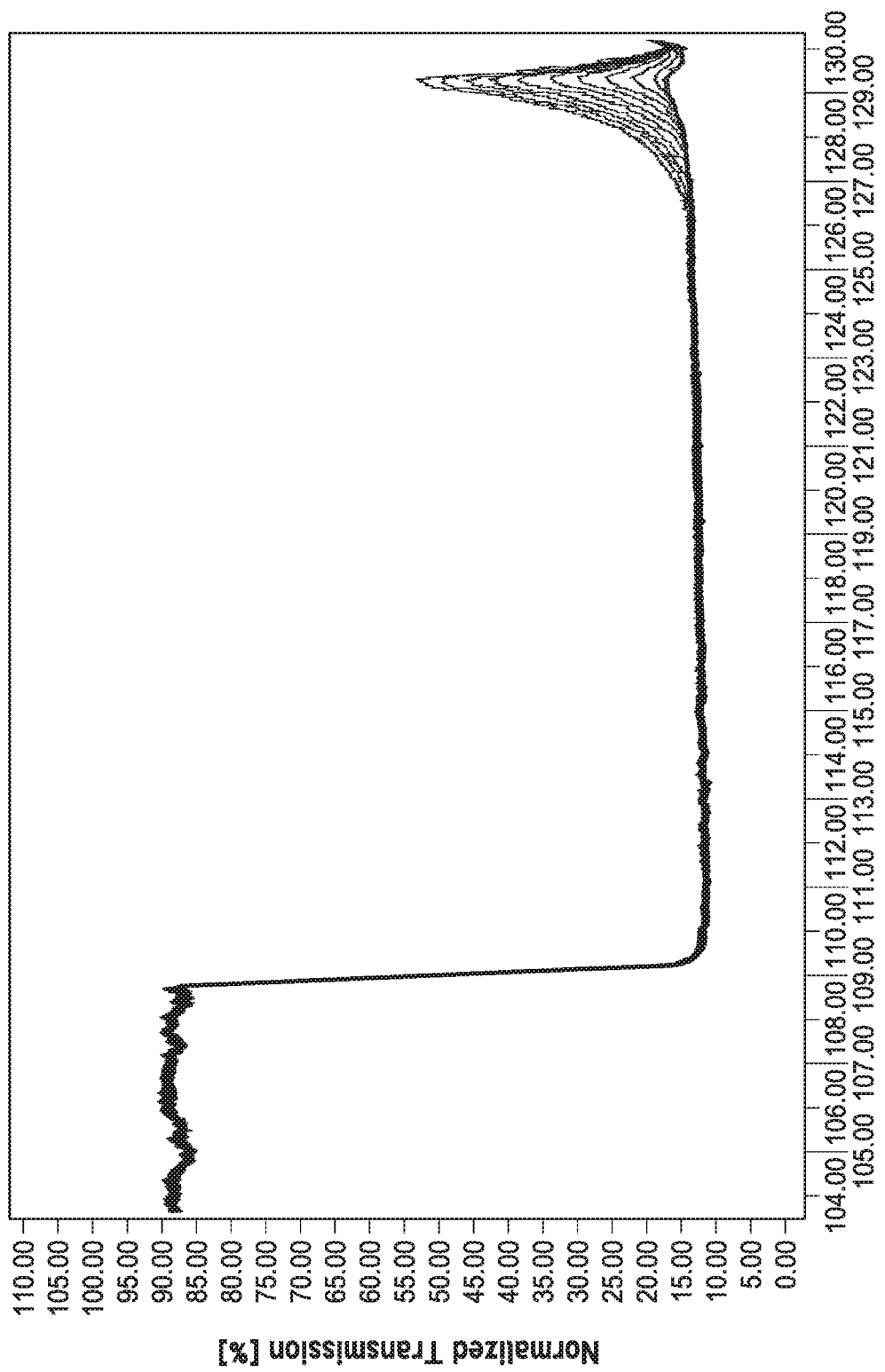

Results. As shown in FIG. 2A, an undiluted sample of the low salt ophthalmic pharmaceutical composition is stable with time. Light transmission (% T) for the sample is approximately 55%. In contrast, as shown in FIG. 2B, the undiluted control eye drop lacking salt-sensitive viscosity modulating polymer is slightly unstable as indicated by the change over time at the distal end of the integrated optical detector of the time-controlled centrifuge. Moreover, the light transmission in the control is significantly lower, having a value of about 12% (% T) prior to the changes which accompany the destabilization of the control. Without wishing to be bound by any theory, it is believed that changes in % T correlate with release of lipid which migrates to the top (i.e., distal end) of the centrifuge chamber, consistent with floating of lipid to the air interface of the aqueous layer of the tear film.

Figure 3A:
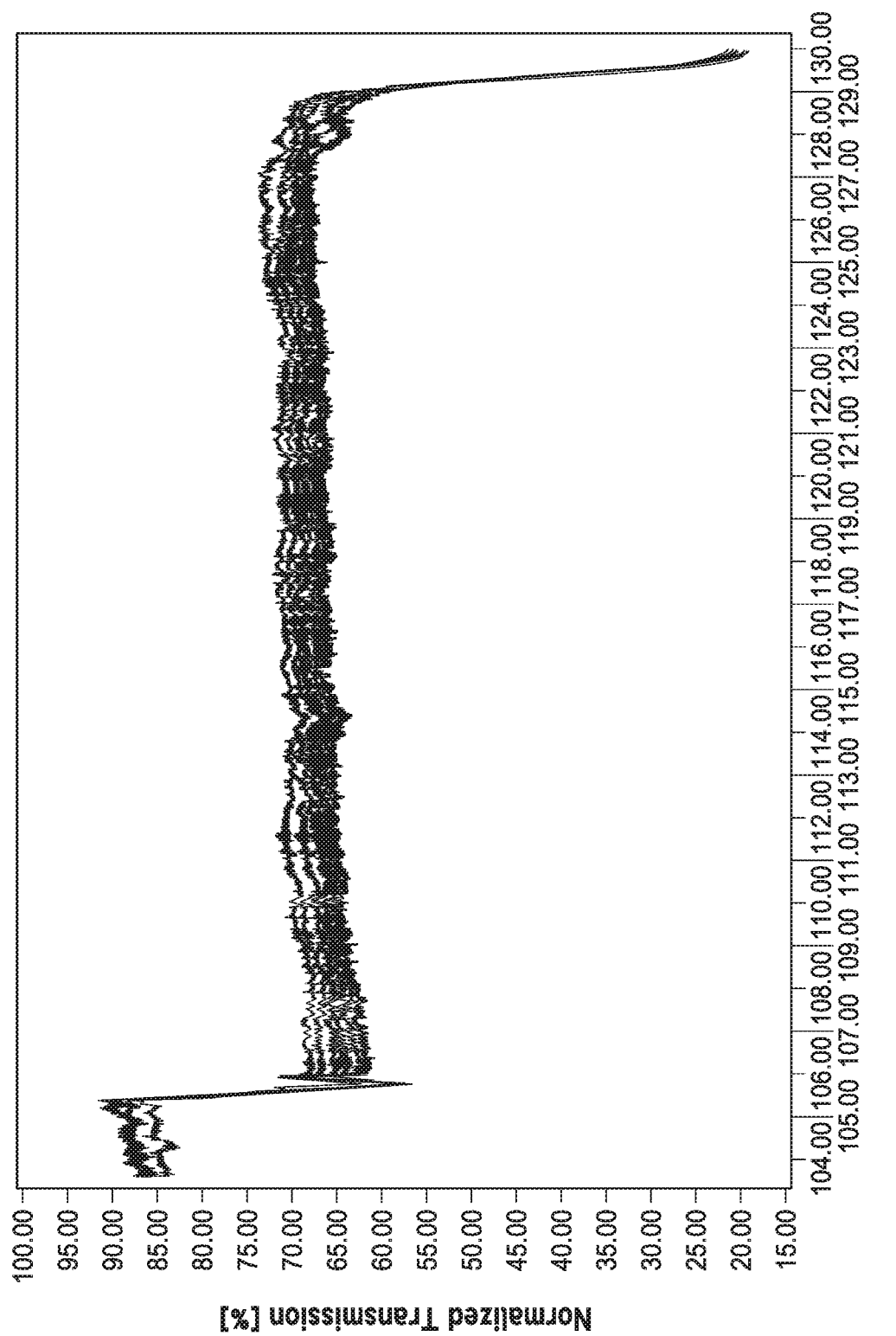
FIGS. 3A-3B depict overlaid real-time integrated optical detector scans in a time-controlled centrifuge of sample (FIG. 3A) and control (FIG. 3B) diluted 1:20 with water, as described in Example 2. Legend: as in FIGS. 2A-2B.
Figure 3B:
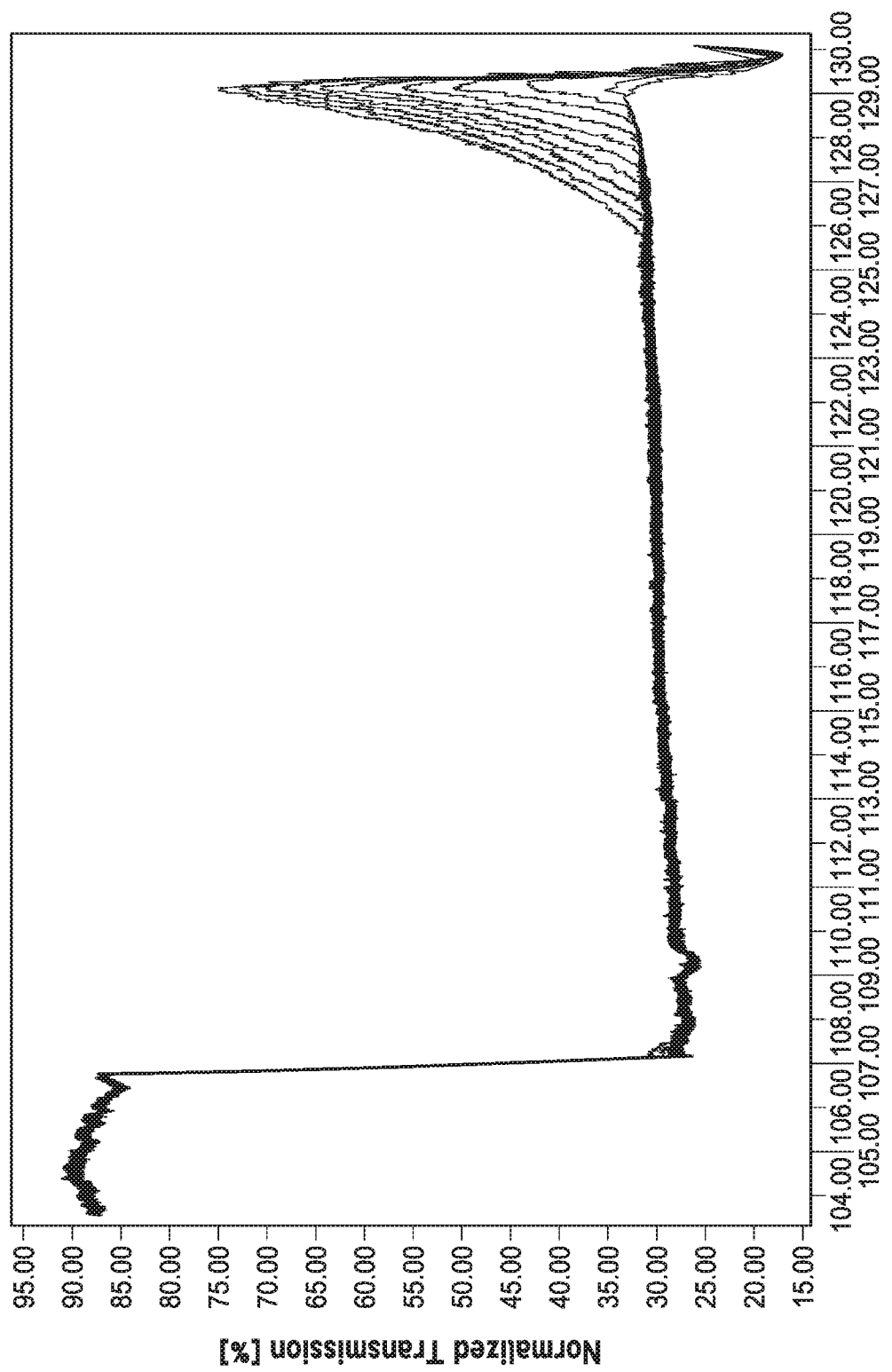

As shown in FIGS. 3A-3B, upon dilution 1:20 with water, both the sample and control show increase in % T due to dilution. Stability in both experiments is similar to that observed in the undiluted state.

Figure 4A:
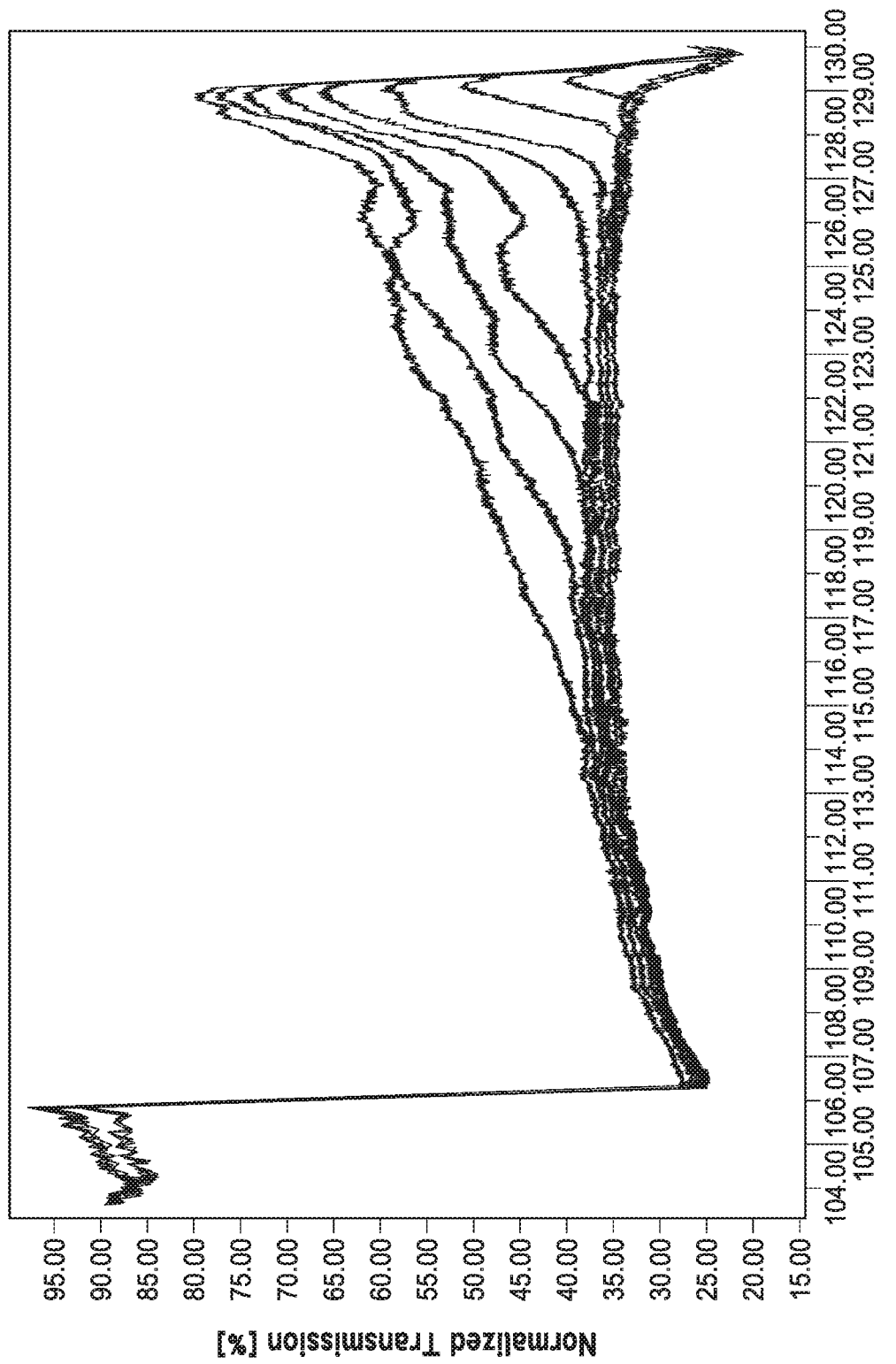
FIGS. 4A-4B depict overlaid real-time integrated optical detector scans in a time-controlled centrifuge of sample (FIG. 4A) and control (FIG. 4B) diluted 1:20 with 9% NaCl solution, as described in Example 2. Legend: as in FIGS. 2A-2B.
Figure 4B:
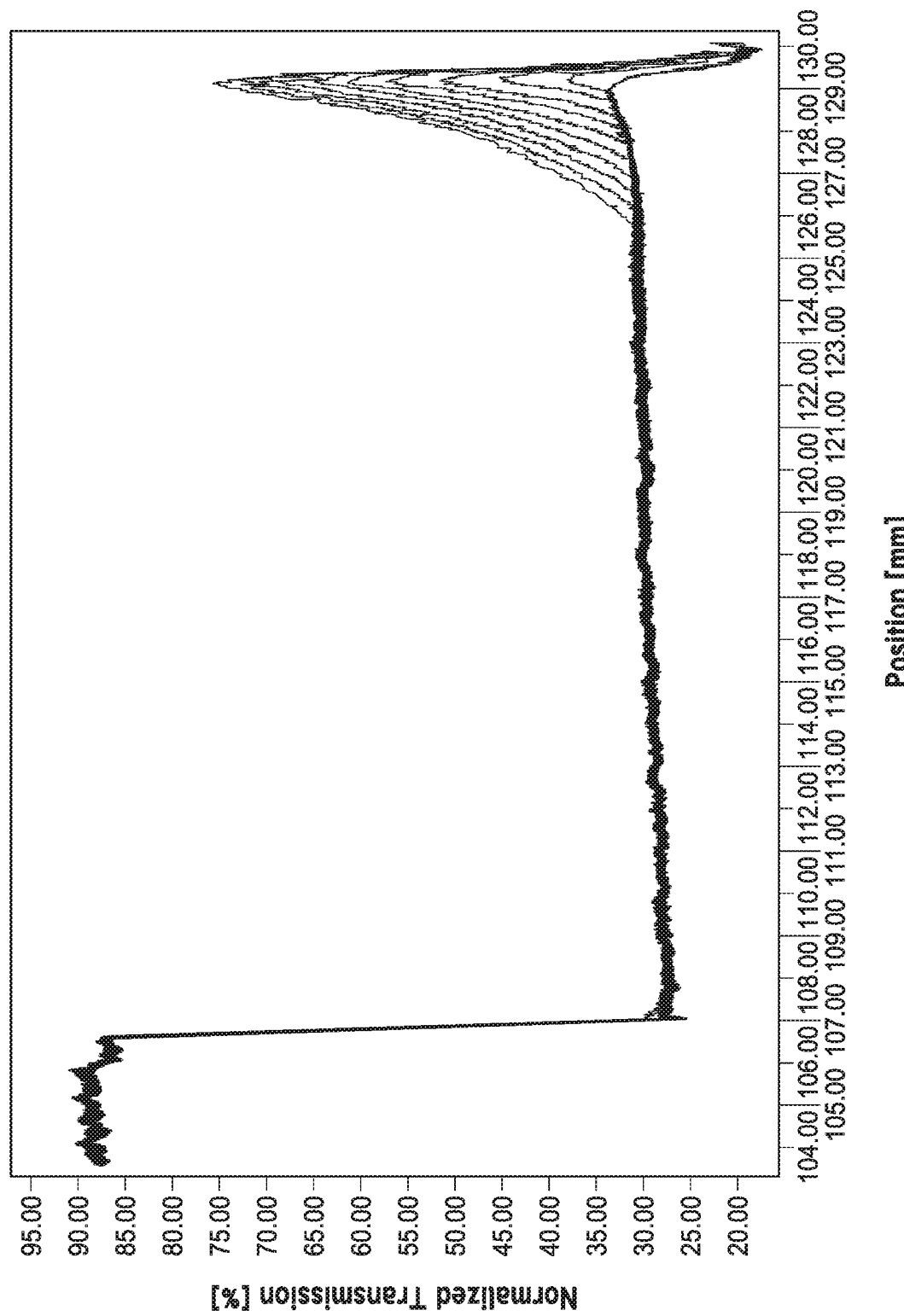

As shown in FIG. 4A, upon dilution 1:20 with 9% NaCl, the sample is significantly destabilized with rapid release of oil and transient drop in % T. In contrast, as shown in FIG. 4B, the stability of the control is similar to that observed with water dilution.

Summary. The low salt ophthalmic pharmaceutical composition sample was stable and uniform in the undiluted state, as occurs in storage prior to use. This demonstrates the surprising benefit of excellent stability and uniformity in storage, while requiring no shaking of the composition prior to instillation. In contrast, the control eye drop lacking salt-sensitive viscosity modulating polymer is slightly unstable in storage. When mixed with salt, the viscosity of the sample dropped significantly. In contrast, the control did not demonstrate a dependence of stability on salt concentration. Without wishing to be bound by any theory, it is believed that the reduction in viscosity in the sample destabilizes the structure of the emulsion, resulting in release of lipid. Accordingly, the use of a salt-sensitive viscosity modulating polymer within the sample increases delivery of lipids at the ocular target.

Example 3. Lipid Droplet Particle Size Upon Dilution with Salt

Lipid particle size in solution can be determined by a variety of techniques known in the art, including e.g., laser diffraction, dynamic image analysis, static image analysis, and dynamic light scattering. The change in lipid droplet size within formulations disclosed herein upon instillation in the eye was determine in model systems by dilution with salt solution.

Methods. Average particle size (lipid droplet size) was determined using a Horiba particle size analysis system (Horiba, Ltd., Fukuoka Japan). The sample composition and salt solutions were as described in Examples 1-2.

Results. Upon dilution with salt solution, the average particle size (i.e., lipid droplet size) was unchanged (data not shown).

Summary. The lipid droplet size of tested formulations does not change upon an increase in salt concentration. Accordingly, the lipid droplets remain sufficiently small to provide effective incorporation of lipid into the tear film.

Example 4. Clinical Studies

Tear breakup time (TBUT) is recognized as a useful procedure in the diagnosis of dry eye syndrome and related conditions. As known in the art, compositions and methods which increase TBUT can be beneficial in the treatment. Thus, clinical studies were conducted which measured TBUT for a low salt ophthalmic pharmaceutical composition disclosed herein. Moreover, the clinical studies included tolerability and comfort assessments, as known in the art.

Methods. The fluorescein tear breakup time procedure was employed, as known in the art.

Results. The low salt ophthalmic pharmaceutical composition set forth in Table 2 above was observed to prolong TBUT. Moreover, the composition demonstrates clinical tolerability and comfort.

Example 5. Clinical Studies

A Multicenter, Investigator-masked, Randomized, 4-Arm, Parallel-group Study to Evaluate the Safety, Efficacy, and Acceptability of a Unit-dose Eye Drop Formulation in Subjects With Dry Eye Disease The objective of the study was to evaluate the safety, efficacy, and acceptability of the formulation of Table 1, but without containing Purite®, referred to as a Next Generation Emulsion Unit-dose or ("NGE UD") in subjects with signs and symptoms of dry eye disease.

Methodology

This was a multicenter, investigator-masked, randomized, active-controlled, 4-arm, parallel group study designed to compare the safety, efficacy, and acceptability of NGE UD to commercially available OPTIVE™ Sensitive Preservative-free Lubricant Eye Drops Unit-dose ("OPTIVE UD"), NGE UD to Next Generation Emulsion Multidose ("NGE MD") (same formulation as Table 1 but with Purite®), and NGE MD to OPTIVE™ Lubricant Eye Drops Multidose ("OPTIVE MD").

The planned study duration was 30 days for each subject and consisted of up to 3 scheduled visits (days 1 [baseline], 7, and 30 [exit]). On day 1, eligible subjects with signs and symptoms of dry eye disease were assigned according to a 2:2:1:1 treatment allocation ratio to use NGE UD, OPTIVE UD, NGE MD, or OPTIVE MD, respectively. The study randomization was stratified by baseline Ocular Surface Disease Index© (OSDI) score (mild/moderate symptoms=score of 18 to 32; severe symptoms=score of >32 to 65). Approximately 300 subjects were to be enrolled at 13 to 14 sites within the USA in order to have 288 completed subjects assuming a dropout rate of approximately 5%. Subjects were instructed to instill 1 to 2 drops of their assigned study product in each eye, as needed, but at least 2 times daily for 30 days.

Number of Subjects (Planned and Enrolled)

Approximately 300 subjects were planned to be enrolled in this study. A total of 315 subjects were enrolled.

Diagnosis and Main Criteria for Eligibility
Diagnosis/Subjects with Signs and Symptoms of Dry Eye Disease
Key Inclusion Criteria:

Male or female subjects, at least 18 years of age, with a baseline (day 1) OSDI score of ≥18 and ≤65 (based on a 0 to 100 scale) were eligible for enrollment. Subjects must have been using topical ophthalmic drops for dry eye at least twice daily, for at least 3 months prior to baseline, on average. If there was daily use of RESTASIS® Cyclosporine Ophthalmic Emulsion, it must have been in use for ≥6 months. Three consecutive tear break-up time (TBUT) tests ≤10 seconds in at least 1 eye at baseline were required. Using the modified National Eye Institute (NEI) Grid, all subjects had to have at least a Grade 1 staining in at least 1 of the 5 zones of the cornea or in at least 1 of the 6 zones of the conjunctiva that is related to dry eye in at least 1 eye at baseline.

Key Exclusion Criteria:

Key exclusion criteria included a Schirmer test (with anesthesia) ≤2 mm in either eye at baseline; corneal or conjunctival staining score of 5 (modified NEI Grid) at baseline in any of the 5 corneal or 6 conjunctival zones of either eye; use of systemic medications that could have affected a dry eye condition or vision, unless that medication had been used at the same dose for at least 3 months prior to study enrollment and the dosage was not expected to change during the course of the study; history of anterior segment surgery or trauma that could have affected corneal sensitivity (eg, cataract surgery, laser-assisted in situ keratomileusis [LASIK], photorefractive keratectomy, or any surgery involving a limbal or corneal incision) within 12 months prior to baseline; and current use of, and/or use within 2 weeks prior to baseline, and/or likely use during the study period of any topical ophthalmic medications (e.g., topical ophthalmic steroids, glaucoma drops, any topical cyclosporine product other than Restasis®. Subjects who discontinued use of daily Restasis® less than 3 months prior to baseline were excluded from the study.

Duration of Treatment: The total duration of exposure to the study product (drops) for each subject was 30 days. The visit schedule consisted of a baseline visit (day 1) and 2 follow-up visits on days 7 (±3 days) and 30/early exit (±7 days).

Efficacy and Safety Measurements
Efficacy: Primary—OSDI Questionnaire Score
  Secondary—TBUT (with fluorescein), corneal staining (modified NEI Grid, with fluorescein), conjunctival staining (modified NEI Grid, with lissamine green), and Schirmer test (with anesthesia)
  Other—Acceptability Questionnaire and Study Product Usage Questionnaire
Safety:
  The safety measures were adverse events, biomicroscopy, and distance visual acuity.
Statistical Methods:

The intent-to-treat (ITT) population consisted of all randomized subjects and was used for analyses of efficacy data based on the treatment randomized. The safety population consisted of all treated subjects and was used for analyses of all safety data based on the actual treatment received. The per-protocol (PP) population consisted of randomized subjects who had no major protocol violations, as determined prior to database lock.

The primary efficacy variable was the change from baseline in OSDI score at day 30 in the ITT population. The primary efficacy analysis was performed on the change from baseline in OSDI score at day 30 via a 2-way analysis of variance (ANOVA) model with treatment and baseline OSDI stratification as the main effects.

Last observation carried forward (LOCF) was used to impute missing data. Noninferiority was tested using a 2-sided confidence interval (CI). The treatment difference and 95% CI in change from baseline in OSDI score at day 30 between NGE UD and OPTIVE UD (NGE UD minus OPTIVE UD) were calculated based on the ANOVA model. Non-inferiority was established if the upper limit of the 95% CI was less than the prespecified margin of 7.3.

The Secondary efficacy measures included TBUT, corneal staining, conjunctival staining, and Schirmer test. The raw values of these measures were summarized for the ITT population, with missing data imputation using LOCF at each scheduled follow-up visit. The treatment difference and 95% CI for between-treatment comparisons were calculated. The treatment differences and 95% CIs in change from baseline in OSDI score at day 30 between NGE UD and NGE MD, NGE MD and OPTIVE MD were also analyzed as secondary efficacy variables.

Acceptability was measured using the Acceptability Questionnaire, and product usage was measured using the Study Product Usage Questionnaire. Comparisons across groups were performed using ANOVA model with treatment and baseline OSDI stratification as the main effects.

The safety variables included adverse events, biomicroscopy, and distance visual acuity. Since both eyes were treated, both eyes were included in the safety analyses. The Medical Dictionary for Regulatory Activities (MedDRA) nomenclature was used to code adverse events. The number and percent of subjects with clinically significant biomicroscopy findings at one or more visits in either eye were tabulated. The overall frequency distribution was analyzed using Pearson's chi-square test. For a clinically significant biomicroscopic finding (more than 1 severity grade increase [worsening] from baseline) with an incidence rate of ≥5% in any treatment group, the mean severity grade and the frequency distribution of severity scores were summarized at each scheduled visit.

Data from the eye with the worst severity at the scheduled visit was tabulated. For distance visual acuity data, the total numbers of letters read correctly were summarized based on the eye with worse change from baseline at each scheduled visit. The frequency distribution was analyzed using Pearson's chi-square test.

A total of 315 subjects were enrolled in the study and included in the ITT population; 105 subjects in the NGE UD group, 103 subjects in the OPTIVE UD group, 51 subjects in the NGE MD group, and 56 subjects in the OPTIVE MD group. Overall, 310 (98.4%) subjects in the ITT population completed the study. Of the subjects included in the per protocol population, 99.3% (303/305) completed the study whereas 98.4% (310/315) of the subjects in the safety population completed the study. A total of 384 subjects were screened of which 69 subjects were screen failures.

In the ITT population, the mean age of all subjects was 54.8 years (standard deviation 14.33) with 83.2% (262/315) of subjects in the >40 years age group. In addition, 81.0% (255/315) of all subjects were female and 84.4% (266/315) were Caucasian.

Efficacy:

The primary efficacy endpoint was met. At day 30, no statistically significant difference was observed between the NGE UD and the OPTIVE UD groups in the mean change from baseline in OSDI score (95% confidence interval [−5.42, 2.51]), in the ITT population. The NGE UD formulation was noninferior to the OPTIVE UD formulation in reducing the severity of symptoms of dryness as measured by the change from baseline in OSDI score.

Similar to the ITT population, there was no statistically significant difference between the NGE UD and OPTIVE UD groups of the PP population in the mean change from baseline in OSDI score at day 30. The 95% confidence interval at the day 30 visit was (−5.72, 2.37); with an upper limit that is lower than the clinically relevant margin of 7.3.

In all 4 treatment groups, there was a statistically significant difference (p<0.001) in the mean change from baseline in OSDI score at the day 7 and day 30 visits for both the ITT and the PP population.

The NGE UD group was noninferior to the NGE MD group in the mean change from baseline in OSDI score at day 30.

The NGE UD group was noninferior to the OPTIVE UD and NGE MD groups in the secondary efficacy measures of TBUT, corneal staining, conjunctival staining, and Schirmer test.

Overall, there were no statistically significant differences between the NGE UD and OPTIVE UD groups, NGE UD and NGE MD groups, or NGE MD and OPTIVE MD groups, in the mean values for each question of the acceptability questionnaire at the day 7 and day 30 visits (except for question 5 in the NGE MD versus OPTIVE MD comparison at day 7 and NGE UD versus NGE MD comparison at day 30), and in the mean number of times per day that the study product was used during the week prior to the day 7 and day 30 visits.

Safety:

At least 1 treatment-emergent adverse event (TEAE) of any causality was reported in 11.4%, 15.5%, 13.7%, and 10.7% of subjects in the NGE UD, OPTIVE UD, NGE MD and OPTIVE MD groups, respectively.

No deaths were reported in the study. Two serious adverse events were reported (bile duct stone [NGE UD group] and ankle fracture [OPTIVE MD group]), none of which were treatment related in the opinion of the investigator.

Overall 3 subjects discontinued from the study due to adverse events, 1 subject each in the NGE UD, NGE MD and OPTIVE MD groups.

Treatment-related TEAE were reported in 4.8%, 8.7%, 7.8%, and 5.4% of subjects in the NGE UD, OPTIVE UD, NGE MD, and OPTIVE MD groups, respectively. The most common treatment-related adverse events (preferred terms) across treatment groups were instillation site pain and vision blurred; NGE UD (3.8%, 2.9%), OPTIVE UD (3.9%, 2.9%), NGE MD (3.9%, 0.0%), and OPTIVE MD (3.6%, 1.8%).

In the majority of the subjects, no change was observed in the distance visual acuity at day 30 for all 4 treatment groups.

CONCLUSIONS

Efficacy: The results of this study demonstrate that the NGE UD formulation is non-inferior to the OPTIVE UD formulation in reducing the severity of symptoms of dryness in subjects with mild to severe dry eye.

Safety: NGE UD appeared to be well tolerated during the study. The most commonly reported treatment-related adverse events were instillation site pain and vision blurred. Throughout the study, there were no treatment-related serious adverse events. The safety profile was consistent with OPTIVE UD, OPTIVE MD, and NGE MD. This is supportive of the safety of the NGE UD formulation in clinical use, and confirms the safety of the NGE MD formulation.

What is claimed is:

1. A low salt ophthalmic pharmaceutical composition useful for the treatment of dry eye or keratoconjunctivitis comprising a sub-micron emulsion, a polymer lubricant, and a salt-sensitive viscosity modulating polymer, wherein said sub-micron emulsion comprises a surfactant and a therapeutic lipid consisting of castor oil.

2. The low salt ophthalmic pharmaceutical composition according to claim 1, wherein said surfactant is a sorbitan ester, wherein said sorbitan ester is polysorbate 80 present at a concentration of about 0.5% (w/w).

3. The low salt ophthalmic pharmaceutical composition according to claim 1, wherein said salt-sensitive viscosity modulating polymer is an acrylate/C10-C30 acrylate crosspolymer having a standard emulsion viscosity between 1,700 and 4,500 cPs and castor oil at a concentration of 0.25% (w/w).

4. The low salt ophthalmic pharmaceutical composition according to claim 1, wherein said polymer lubricant is carboxymethylcellulose sodium present at a concentration of about 0.5% (w/w).

5. The low salt ophthalmic pharmaceutical composition according to claim 1, further comprising a compatible solute.

6. The low salt ophthalmic pharmaceutical composition according to claim 5, wherein said compatible solute is erythritol or levocarnitine.

7. The low salt ophthalmic pharmaceutical composition according to claim 6 comprising erythritol at a concentration of about 0.25% (w/w) and levocarnitine at a concentration of about 0.25% (w/w).

8. The low salt ophthalmic pharmaceutical composition according to claim 1, further comprising a tonicity agent, wherein said tonicity agent is glycerin present at a concentration of about 1.0% (w/w).

9. The low salt ophthalmic pharmaceutical composition according to claim 1, further comprising a preservative.

10. The low salt ophthalmic pharmaceutical composition according to claim 9, wherein said preservative is a stabilized oxychloro complex present at a concentration of about 0.01% (w/w).

11. The low salt ophthalmic pharmaceutical composition according to claim 10 further comprising a buffer.

12. The low salt ophthalmic pharmaceutical composition according to claim 11, wherein said buffer is boric acid present at a concentration of about 0.6% (w/w).

13. The low salt ophthalmic pharmaceutical composition according to claim 12 further comprising a pH adjustment agent.

14. The low salt ophthalmic pharmaceutical composition according to claim 13, wherein said pH adjustment agent is NaOH.

15. The low salt ophthalmic pharmaceutical composition according to claim 13 having pH of about 7.3.

16. A low salt ophthalmic pharmaceutical composition wherein the composition is a sub-micron emulsion comprising:
    a therapeutic lipid consisting of castor oil at a concentration of about 0.25% (w/w);
    polysorbate 80 at a concentration of about 0.5% (w/w);
    acrylate/C10-C30 acrylate crosspolymer at a concentration of about 0.1% (w/w),
    wherein said acrylate/C10-C30 acrylate crosspolymer has a standard emulsion viscosity between 1,700 and 4,500 cPs;
    carboxymethylcellulose sodium at a concentration of about 0.5% (w/w);
    glycerin at a concentration of about 1.0% (w/w);
    a stabilized oxychloro complex preservative at a concentration of about 0.01% (w/w);
    boric acid at a concentration of about 0.6% (w/w);
    erythritol at a concentration of about 0.25% (w/w);
    levocarnitine at a concentration of about 0.25% (w/w);
    NaOH; and
    water.

17. A method for treating dry eye syndrome comprising:
    administering to a subject in need of treatment of dry eye syndrome a low salt
    ophthalmic pharmaceutical composition according to claim 16;
    thereby treating said dry eye syndrome.

18. The method of claim 17 wherein the ophthalmic composition is applied at least once a day to treat dry eye.

19. The method of claim 18 wherein the ophthalmic composition reduces pain and inflammation associated with dry eye.

* * * * *